United States Patent
Rudie et al.

[11] Patent Number: 5,843,144
[45] Date of Patent: Dec. 1, 1998

[54] METHOD FOR TREATING BENIGN PROSTATIC HYPERPLASIA WITH THERMAL THERAPY

[75] Inventors: Eric N. Rudie, Maple Grove, Minn.; Mitchell Dann, Jackson, Wyo.; John M. Reid, Minnetrista, Minn.; Bruce H. Neilson, Brooklyn Park, Minn.; James V. Kauphusman, Champlin, Minn.; James E. Burgett, Maple Grove, Minn.; Stanley E. Kluge, Albertville, Minn.; Steven W. Norsted, Eden Prairie, Minn.

[73] Assignee: Urologix, Inc., Minneapolis, Minn.

[21] Appl. No.: 494,320

[22] Filed: Jun. 26, 1995

[51] Int. Cl.[6] .................................................... A61N 5/02
[52] U.S. Cl. .......................... 607/101; 607/102; 607/105; 607/113; 607/116; 607/156
[58] Field of Search ......................... 128/736, 772; 604/53, 95; 600/2; 606/27, 41, 28, 33; 607/101, 96, 102, 105, 113, 116, 156

[56] References Cited

U.S. PATENT DOCUMENTS

| | | | |
|---|---|---|---|
| 2,407,690 | 9/1946 | Southworth | 128/422 |
| 2,642,874 | 6/1953 | Keeling | 128/349 |
| 2,813,531 | 11/1957 | Lee | 128/350 |
| 3,125,096 | 3/1964 | Antiles et al. | 128/401 |
| 3,228,400 | 1/1966 | Armao | 128/303.1 |
| 4,140,130 | 2/1979 | Storm, III | 128/404 |
| 4,148,005 | 4/1979 | Larsen et al. | 338/28 |
| 4,154,246 | 5/1979 | LeVeen | 128/784 |
| 4,162,500 | 7/1979 | Jacobi et al. | 343/772 |
| 4,190,053 | 2/1980 | Sterzer | 128/399 |
| 4,204,549 | 5/1980 | Paglione | 128/784 |
| 4,253,469 | 3/1981 | Aslan | 128/736 |
| 4,285,346 | 8/1981 | Armitage | 128/422 |
| 4,290,435 | 9/1981 | Waggott | 128/800 |
| 4,311,154 | 1/1982 | Sterzer et al. | 128/804 |
| 4,312,364 | 1/1982 | Convert et al. | 128/804 |
| 4,375,220 | 3/1983 | Matvias | 128/804 |
| 4,448,198 | 5/1984 | Turner | 128/422 |
| 4,469,103 | 9/1984 | Barrett | 128/400 |
| 4,497,324 | 2/1985 | Sullivant et al. | 128/736 |
| 4,557,272 | 12/1985 | Carr | 128/736 |
| 4,583,556 | 4/1986 | Hines et al. | 128/804 |
| 4,601,296 | 7/1986 | Yerushalmi | 128/804 |
| 4,612,940 | 9/1986 | Kasevich et al. | 128/804 |
| 4,632,127 | 12/1986 | Sterzer | 128/804 |
| 4,643,186 | 2/1987 | Rosen et al. | 128/303.1 |
| 4,662,383 | 5/1987 | Sogawa et al. | 128/784 |
| 4,669,475 | 6/1987 | Turner | 128/399 |
| 4,672,963 | 6/1987 | Barken | 128/303.1 |
| 4,676,258 | 6/1987 | Inokuchi et al. | 128/804 |
| 4,681,122 | 7/1987 | Winters et al. | 128/736 |
| 4,690,156 | 9/1987 | Kikuchi et al. | 128/804 |
| 4,700,716 | 10/1987 | Kasevich et al. | 128/804 |
| 4,708,718 | 11/1987 | Daniels | 604/53 |
| 4,709,698 | 12/1987 | Johnston et al. | 128/303.12 |
| 4,712,559 | 12/1987 | Turner | 128/422 |
| 4,732,161 | 3/1988 | Azam et al. | 128/784 |
| 4,776,086 | 10/1988 | Kasevich et al. | 29/828 |
| 4,777,951 | 10/1988 | Cribier et al. | 128/344 |
| 4,798,215 | 1/1989 | Turner | 128/804 |
| 4,800,899 | 1/1989 | Elliott | 128/804 |
| 4,808,164 | 2/1989 | Hess | 604/95 |
| 4,813,429 | 3/1989 | Eshel et al. | 128/736 |
| 4,821,725 | 4/1989 | Azam et al. | 128/420 A |
| 4,823,812 | 4/1989 | Eshel et al. | 128/804 |
| 4,825,880 | 5/1989 | Stauffer et al. | 128/804 |
| 4,832,023 | 5/1989 | Murphy-Chutorian et al. | 128/303.1 |
| 4,841,988 | 6/1989 | Fetter et al. | 128/804 |
| 4,860,752 | 8/1989 | Turner | 128/422 |
| 4,865,047 | 9/1989 | Chou et al. | 128/784 |
| 4,878,492 | 11/1989 | Sinofsky et al. | 128/303.1 |
| 4,907,589 | 3/1990 | Cosman | 606/34 |
| 4,924,863 | 5/1990 | Sterzer | 606/27 |
| 4,927,413 | 5/1990 | Hess | 604/95 |
| 4,932,420 | 6/1990 | Goldstolm | 128/804 |
| 4,945,318 | 7/1990 | Kabachinski et al. | 333/12 |
| 4,946,449 | 8/1990 | Davis, Jr. | 604/256 |
| 4,955,377 | 9/1990 | Lennox et al. | 128/401 |
| 4,961,738 | 10/1990 | Mackin | 606/15 |
| 4,967,765 | 11/1990 | Turner et al. | 128/785 |
| 4,993,430 | 2/1991 | Shimoyama et al. | 128/784 |
| 4,994,014 | 2/1991 | Gordon | 600/13 |
| 4,998,933 | 3/1991 | Eggers et al. | 606/41 |
| 5,003,991 | 4/1991 | Takayama et al. | 128/784 |
| 5,007,437 | 4/1991 | Sterzer | 428/786 |
| 5,026,959 | 6/1991 | Ito et al. | 219/10.55 A |
| 5,045,056 | 9/1991 | Behl | 604/49 |
| 5,056,531 | 10/1991 | Shimoyama | 128/784 |

| | | | |
|---|---|---|---|
| 5,057,106 | 10/1991 | Kasevich et al. | 606/33 |
| 5,097,845 | 3/1992 | Fetter et al. | 128/804 |
| 5,106,360 | 4/1992 | Ishiwara et al. | 600/2 |
| 5,151,100 | 9/1992 | Abele et al. | 606/28 |
| 5,234,004 | 8/1993 | Hascoet et al. | 607/116 |
| 5,300,099 | 4/1994 | Rudie | 607/101 |
| 5,304,214 | 4/1994 | DeFord et al. | 607/105 |
| 5,312,392 | 5/1994 | Hofstetter et al. | 606/2 |
| 5,323,781 | 6/1994 | Ideker et al. | 128/660.03 |
| 5,326,343 | 7/1994 | Rudie et al. | 607/101 |
| 5,330,518 | 7/1994 | Neilson et al. | 607/101 |
| 5,344,398 | 9/1994 | Hara | 604/96 |
| 5,344,435 | 9/1994 | Turner et al. | 607/101 |
| 5,364,392 | 11/1994 | Warner et al. | 606/34 |
| 5,370,676 | 12/1994 | Sozanski et al. | 607/101 |
| 5,370,677 | 12/1994 | Rudie et al. | 607/101 |
| 5,370,678 | 12/1994 | Edwards et al. | 607/101 |
| 5,391,196 | 2/1995 | Devonec | 607/96 |
| 5,413,588 | 5/1995 | Rudie et al. | 607/101 |
| 5,464,437 | 11/1995 | Reid et al. | 607/101 |
| 5,464,445 | 11/1995 | Rudie et al. | 607/101 |
| 5,496,271 | 3/1996 | Burton | 604/54 |
| 5,509,929 | 4/1996 | Hascoet et al. | 607/101 |
| 5,545,137 | 8/1996 | Rudie et al. | 604/96 |

FOREIGN PATENT DOCUMENTS

| | | |
|---|---|---|
| 0 105 677 | 9/1983 | European Pat. Off. . |
| 0 370 890 A1 | 11/1988 | European Pat. Off. . |
| 0 459 535 A2 | 11/1988 | European Pat. Off. . |
| 0 462 302 A1 | 6/1990 | European Pat. Off. . |
| 0 519 958 B1 | 3/1991 | European Pat. Off. . |
| 0 485 323 A1 | 11/1991 | European Pat. Off. . |
| 0 629 382 A1 | 8/1993 | European Pat. Off. . |
| 0 597 463 A2 | 11/1993 | European Pat. Off. . |
| 0 628 288 A2 | 5/1994 | European Pat. Off. . |
| 58-70219 Sho | 5/1981 | Japan . |
| 62-122661 | 11/1985 | Japan . |
| 63-177867 | 1/1987 | Japan . |
| WO 81/03616 | 6/1981 | WIPO . |
| WO 86-01919 | 9/1985 | WIPO . |
| WO 91/13650 | 9/1991 | WIPO . |
| WO 94/02204 | 7/1993 | WIPO . |
| WO 94/22384 | 3/1994 | WIPO . |
| WO 94/26178 | 5/1994 | WIPO . |
| WO 94/26186 | 5/1994 | WIPO . |
| WO 94/26187 | 5/1994 | WIPO . |
| WO 94/26188 | 5/1994 | WIPO . |

OTHER PUBLICATIONS

Debicki et al., *Cooled microwave transrectal applicator with adjustable directional beam for prostate treatment*, Int. J. Hyperthermia, 1995, vol. 11, No. 1, 95–108.

Thayne R. Larson et al., *An Accurate Technique for Detailed Prostatic Interstitial Temperature–Mapping in Patients Receiving Microwave Thermal Treatment*, Journal of Endourology, vol. 9, No. 4, Aug. 1995.

Stanley B. Field, *Hyperthermia in the treatment of cancer*, 1985 Douglas Lea Memorial Lecture, pp. 789–811.

A. Yerushalmi et al., *Local Microwave Hyperthermia in the Treatment of Carcinoma of the Prostate*, Oncology 43: 299–305 (1986).

E. Perez–Castro, *International consultation on BPH by WHO. Report of the subgroup on other non–medical treatement*, Arch. Esp. de Urol. 45.1, 1992.

Valdagni, Amichetti: *Clinical Hyperthermia: Five Year's Experience*, Strahlentherapie und Onkologie 163 (1987), 443–445.

Astrahan et la., *Thermometry Characteristics of the BSD Interstitial Hyperthermia Applicator*, Endocurietherapy/Hyperthermia Oncology, Jul. 1987, vol. 3, pp. 153–160.

Astrahan et al., *A Technique for Combining Microwave Hyperthermia with Intraluminal Brachytherapy of the Oesophagus*, International Journal of Hyperthermia, vol. 5, No. 1, pp. 37–51, Jan.–Feb. 1989.

Astrahan et al., *Heating Characteristics of a Helical Microwave Applicator for Transurethral Hyperthermia of Benign Prostatic Hyperplasia*, Int. J. Hyperthermia, 1991, vol. 7, No. 1, pp. 141–155.

R.T. Constable et al., *Perturbation of the temperature distribution in microwave irradiated tissue due to the presence of metallic thermometers*, Med. Phys. 14(3), May/Jun. 1987.

Giovanella et al., *Selective Lethal Effect of Supranormal Temperatures on Human Neoplastic Cells*, Cancer Research vol. 36, 3944–3950, Nov. 1976.

Harada et al., *Microwave Surgical Treatment of Diseases of Prostate*, Urol, Dec. 1985, vol. 26, No. 6, pp. 572–576.

Harada et al., *Microwave Surgical Treatment of the Prostate: Clinical Application of Microwave Surgery as a Tool for Improved Prostatic Electrosection*, Urol Int 1987, vol. 42, pp. 127–131.

Leybovich et al., *Intracavitary Hyperthermia: A Newly Designed Applicator for Tracheal Tumors*, Endourcurietherapy–Hyperthermia Oncology 1987, vol. 3, pp. 23–29, Jan.

Li, Ding–Jui et al., *Design and Thermometry of an Intracavitary Microwave Applicator Suitable for Treatment of Some Vaginal and Rectal Cancers*, J. Radiation Oncology Biol. Phys., vol. 10, pp. 2155–2162, 1984.

Linder et al., *Local Hyperthermia for the Treatment of Urinary Retention Due to Benign Prostatic Hypertrophy*, J. Urol, Apr. 1989, vol. 141, p. 355A, Abstract #741 AUA 84th Annual Meeting, May 1989.

Manning et al., *Clinical Hyperthermia: Results of a Phase I Trial Employing Hyperthermia Alone or on Combination with External Beam or Interstitial Radiotherapy*, Cancer 1982, vol. 49, pp. 205–216.

Marmor et al., *Combined Radiation and Hyperthermia in Superficial Human Tumors*, Cancer 1980, vol 46, pp. 1986–1991.

Marmor et al., *Clinical Trial of Ultrasound (US) Induced Local Hyperthermia (HT)*, Abstracts #C–94, Fourteenth Annual Meeting of the American Society of Clinical Oncology 1978, vol. 19, p. 330.

Yerushalmi et al., *Benign Prostatic Hyperplasia—Treatment with Localized Deep Microwave Hyperthermia*, VIIth Meeting of the European Society for Hyperthermic Oncology (ESHO), Paris, Sep. 16–18, 1985 pp. 523, 557 (Nr. 9).

Overgaard, *Fractionated Radiation and Hyperthermia: Experimental and Clinical Stuides*, Cancer 1981, vol. 48, pp. 1116–1123.

Sathiaseelan et al., *A Clinical Microwave Hyperthermia System with Multipoint Sealtime Thermal Dosimetry*, British Journal Radiology, 1985, vol. 58, pp. 1187–1195.

Strohmaier et al., *Local Microwave Hyperthermia of Benign Prostatic Hyperplasia*, The Journal of Urology 1990, vol. 144, pp. 913–917.

Turner, *Recent Developments and Work in Progress*, Strahlentherapie und Onkologie, vol. 163 (1987), pp. 422–424.

Yerushalmi, *Combined Treatment of a Solid Tumour by Local Hyperthermia and Actinomycin D*, Br. J. Cancer (1978), vol. 37, pp. 827–832.

Yerushalmi et al., *Localized Deep Microwave Hyperthermia in the Treatment of Poor Operative Risk Patients with Benign Prostatic Hyperplasia*, The Journal of Urology, vol. 133, May 1985, pp. 873–876.

Yerushalmi, *Localized, Non–Invasive Deep Microwave Hyperthermia for the Treatment of Prostatic Tumors: The First 5 Years*, Cancer Research, vol. 107, pp. 141–146, 1988.

Yerushalmi, *Use of Local Hyperthermia for the Treatment of Benign Prosatic Hyperplasia*, Concensus on Hyperthermia for the 1990s, pp. 167–176, 1990.

Michael L. Blute, *Transurethral Microwave Thermotherapy for Benign Prostatic Hypertrophy*, Mediguide® to Urology, vol. 4, Issue 6, pp. 1–8, 1991.

Anghileri et al., *Hyperthermia in Cancer Treatment*, vol. III, 1986 by CRC Press, Inc..

Astrahan et al., *Microwave Applicator for Transurethral Hyperthermia of Benign Prostatic Hyperplasia*, Int. J. Hyperthermia, 1989, vol. 5, No. 3, pp. 283–296.

Astrahan et al., *Interstitial Temperature Measurements During Transurethral Microwave Hyperthermia*, The Journal of Urology, vol. 145, pp. 304–308, Feb. 1991.

Baert, et al., *Treatment Response with Transurethral Microwave Hyperthermia in Different Forms of Benign Prostatic Hyperplasia: A Preliminary Report*, The Prostate 18:315–320 (1991), Wiley–Liss, Inc. 1991.

Baert, et al., *Transurethral Microwave Hyperthermia for Benign Prostatic Hyperplasia: Preliminary Clinical and Pathological Results*, The Journal of Urology, vol. 144, Dec., pp. 1383–1387, 1990.

M.L. Blute, et al., *Transurethral Microwave Thermotherapy for Prostatism: Early Mayo Foundation Experience*, Mayo Clinic Proceedings, vol. 67, pp. 417–495, May 1992.

Carter et al., *Single–Session Transurethral Microwave Thermotherapy for the Treatment of Benign Prostatic Obstruction*, Journal of Endourology, vol., 5 No. 2, 1991.

Cavaliere et al., *Selective Heat Sensitivity of Cancer Cells*, Cancer, Sep. 1967, vol. 20, pp. 1351–1381.

T.C. Cetas et al., *Thermometry consideration in localized hyperthermia*, Med. Phys. 5(2), Mar./Apr. 1978.

Debicki et al., *Superficial and Intraurethral Applicators for Microwave Hyperthermia*, Consensus on Hypertherma for the 1990s, pp. 321–326, 1990.

Devonec et al., *Transurethral Microwave Heating of the Prostate—Or from Hyperthermia to Thermotherapy*, Journal of Endourology, vol. 5, No. 2, pp. 129–135, 1991.

Marian et al., *Long Term Results of Transurethral Microwave Therapy (TUMT) in Patients with Benign Prostatic Hypertrophy*, The Journal of Urology, AUA Eighty–Sixth Annual Meeting, Jun. 2–6, 1991.

Devonec et al. *Clinical Response to Transurethral Microwave is Thermal Dose Dependant*, Eur Urol. 1993, vol. 23, pp. 267–274.

Harada et al., *Hyperthermic Treatment with Intravesical Microwave Radiation for Bladder Cancer*, 1984.

Harada et al., *Transcystoscopic Intracavitary Irradiation for Carcinoma of the Bladder: Technique and Preliminary Results*, Urol. Oct. 1987, vol. 138, No. 4, pp. 771–775.

James et al., *The Effect of Insertion Depth on the Theoretical SAR Patterns of 915 MHz Dipole Antenna Arrays for Hyperthermia*, Int J. Hyperthermia 1989, vol. 5, No. 6, pp. 733–747.

Kaver et al., *The Effect of Hyperthermia on Human Prostatic Carcinoma Cell Lines: Evaluation in Vitro*, J Urol 1989, vol. 141, pp. 1025–1027.

Larson et al., *Accurate Prostatic Thermal Mapping in 11 Patients Treated with the Urologix T3 System: Understanding the Decay of Temperatures*, 11th World Congress on Endourology, Abstract, Oct. 20–23, 1993.

Leib et al., *Histopathological Observations in the Canine Prostate Treated by Local Microwave Hyperthermia*, Prostate 1986, vol. 8, pp. 93–102.

Linder et al., *Local Hyperthermia of the Prostate Gland for the Treatment of Benign Prostatic Hypertrophy and Urinary Retention*, Br J. Urol 1987, vol. 60, pp. 567–571.

Linder et al., *Local Hyperthermia of the Prostate Gland for the Treatment of Benign Prostatic Hypertrophy and Urinary Retention*, Br J Urol 1990, vol. 65, pp. 201–203.

Linder et al., *Serum Prostate Specific Antigen Levels During Hyperthermia Treatment of Benign Prostatic Hyperplasia*, J. Urol 1990, vol. 144, pp. 1388–1389.

Llinder et al., *Complications in Hyperthermia Treatment of Benign Prostatic Hyperplasia*, J Urol 1990, vol. 144, pp. 1390–1392.

Magin, R. L. et al., *Thermal Destruction of the Canine Prostate by High Intensity Microwaves*, Journal of Surgical Resarch 29, 265–275 (1980).

Marmor, *Interactions of Hyperthermia and Chemotherapy in Animals*, Cancer Research 1979, vol. 39, pp. 2269–2276.

McNeal, *The Prostate Gland: Morphology and Pathobiology*, Monographs in Urology 1988, pp. 36–54.

Mendecki et al., *Microwave Applicators for Localized Hyperthermia Treatment of Malignant Tumors*, J. Bioengineering 1977, vol. 1, pp. 511–518.

Overgaard, *Effect of Hyperthermia on Malignant Cells in Vivo; A Review and Hypothesis*, Cancer 1977, vol. 39, pp. 2637–2646.

Roehrborn et al., *Temperature Mapping in the Canine Prostate During Transurethrally–Applied Local Microwave Hyperthermia*, The Prostate 1992, vol. 20, pp. 97–104.

Salles–Cunha et al., *Steady Magnetic Fields in Noninvasive Electromagnetic Flowmetry*, Proceedings of the IEEE, vol. 68, No. 1, Jan. 1980.

Samulski et al., *Temperature Measurements in High Thermal Gradients: II. Analysis of Conduction Effects*, Int J. Radiation Oncology Biol Phys 1985, vol. 11, pp. 963–971.

Sapozink et al., *Introduction to Hyperthermia Device Evaluation*, Int. J. Hyperthermia, 1988, vol. 4, No. 1, pp. 1–15.

Sapozink et al., *Transurethral Hyperthermia for Benign Prostatic Hyperplasia: Preliminary Clinical Results*, Journal of Urology, May 1990, vol. 143, pp. 944–950.

Saranga et al., *Local Microwave Hyperthermia in the Treatment of Benign Prostatic Hypertrophy*, British Journal of Urology, 1990, vol. 65, pp. 349–353.

Satoh et al., *Implantable Helical Coil Microwave Antenna for Interstitial Hyperthermia*, Int. J. Hyperthermia, 1988, vol. 4, No. 5, pp. 497–512.

Scheiblich et al., *Radiofrequency–Induced Hyperthermia in the Prostate*, Journal of Microwave Power, pp. 472–478.

Servadio et al., *Further Observations on the Use of Local Hyperthermia for the Treatment of Diseases of the Prostate in Man*, Ur. Urol. 1986, vol. 12, pp. 38–40.

Servadio et al., *Local Thermotherapy of the Benign Prostate: A 1–Year Follow–Up*, Eur Urol 1990, vol. 18, pp. 169–173.

Servadio et al., *Chronic Abacterial Prostatitis and Hyperthermia: A Possible New Treatment?*, British Journal of Urology, 1991, vol. 67, pp. 308–311.

Song, *Effect of Hyperthermia on Vascular Functions of Normal Tissues and Experimental Tumors: Brief Communication*, J. Natl. Cancer Inst., vol. 60, No. 3, Mar. 1978.

Margerger et al., *Other Non–Medical Therapies (Excluding Lasers) in the Treatment of BPH*, pp. 453–466.

Perachino et al., *Does Transurethral Thermotherapy Induce a Long–Term Alpha Blockade?*, Eur Urol 1993, vol. 23, pp. 299–301.

Watson, *Heat and the Prostate*, Inst. of Urol, 1993, vol. 23 (suppl 1), pp. 60–62.

de la Rosette et al., *Clinical Results with Microwave Thermotherapy of Benign Prostatic Hyperplasia*, Eur Urol 1993, vol. 23 (suppl 1), pp. 68–71.

McNeal, *The Prostate and Prostatic Urethra: A Morphologic Synthesis*, The Journal of Urology, 1972, vol. 107, pp. 1008–1016.

Stawarz et al., *A Comparison of Transurethral and Transrectal Microwave Hyperthermia in Poor Surgical Risk Benign Prostatic Hyperplasia Patients*, The Journal of Urology 1991, vol. 146, pp. 353–357.

Sterzer, *Localized Hyperthermia Treatment of Cancer*, 1981.

Strohbehn et al., *Evaluation of an Invasive Microwave Antenna System for Heating Deep–Seated Tumors*, pp. 489–491, National Cancer Inst., Jun. 1982.

Strohmaier et al., *Histological Effects of Local Microwave Hyperthermia in Prostatic Cancer*, Int. J. Hyperthermia, 1991, vol. 7, No. 1, pp. 27–33.

Sugaar et al., *A Histopathologic Study on the Effects of Radiofrequency Thermotherapy on Malignant Tumors of the Lung*, American Cancer Society, 1979, vol. 43, pp. 767–783.

Tabuse, *A New Operative Procedure of Hepatic Surgery Using a Microwave Tissue Coagulator*, Arch Jap Chir, vol. 48 (2), pp. 160–172, Mar. 1979.

Taylor, *Implantable Radiators for Cancer Therapy by Microwave Hyperthermia*, Proceedings of the IEEE, vol. 68, No. 1, Jan. 1980.

Trembly, *The Effects of Driving Frequency and Antenna Length on Power Deposition Within a Microwave Antenna Array Used for Hyperthermia*, IEEE Transactions on Biomedical Engineering, vol., BME–32, No. 2, Feb. 1985.

Tucker et al., *The In Vivo Effect of Regional Hyperthermia on Dunning R3327 Prostatic Tumor*, The Prostate, vol. 18, pp. 321–329, (1991).

Turner, *Interstitial EM Applicator/Temperature Probes*, IEEE/Eighth Annual Conference of the Engineering in Medicine and Biology Society, 1986.

Turner, *Interstitial Equal–Phased Arrays for EM Hyperthermia*, IEEE, 1986, vol. MTT–34, No. 5, May 1986.

Weinbaum et al., *Heat Transfer in Living Tissue: The Search for a Blood–Tissue Energy Equation and the Local Thermal Microvascular Control Mechanism*, BMES Bulletin, vol. 16, No. 3, pp. 38–43, 1992.

Wu et al., *Performance Charateristics of a Helical Microwave Interstitial Antenna for Local Hyperthermia*, Med. Phys., vol. 14, No. 2, Mar./Apr. 1987, pp. 235–237.

Xu et al., *Transurethral Thermal Therapy (T3) for the Treatment of Benign Prostatic Hyperplasia (BPH) in the Canine: Analysis Using Pennes Bioheat Equation*, Adv. in Bioheat and Mass Transfer 1993 ASME Winter Annual Meeting, HTD–vol. 268, pp. 31–35.

Yerushalmi et al., *Normal Tissue Response to Localized Deep Microwave Hyperthermia in the Rabbit's Prostate: A preclinical Study*, Int. J. Radiation Oncology Biol Phys 1982, vol. 9, pp. 77–82.

Yerushalmi et al., *Local Hyperthermia for Treatment of Carcinoma of the Prostate: A Preliminary Report*, The Prostate, vol. 3, pp. 623–630, 1982.

Yerushalmi, *Localized Deep Microwave Hyperthermia (LDMWH) for BPH: Comparison of Short & Long Term Results*, The Journal of Urology, Apr. 1987, p. 358A.

Zerbib et al., *Localized Hyperthermia Versus the Sham Procedure in Obstructive Benign Hyperplasia of the jProstate: A Prospective Randomized Study*, J Urol 1992, vol. 147, pp. 1048–1052.

*A Comparison of Transurethral and Transrectal Microwave Hyperthermia in Poor Surgical Risk Benign Prostatic Hyperplasia Patients*, by B. Stawarz et al., vol. 146, pp. 353–357.

A. Corica et al., *Prostate Thermal Ablation with Urethral Cooling Using the Urologix T3 System—The Early Mendoza Experience*, Abstract: 12th World Congress on Endourology and SWL 8th Annual Frontiers in Endourology 10th Basic Research Symposium, Dec. 2–6, 1994, St. Louis, MO.

T. Larson et al., *Pathological Comparison of Human Prostate Between Treatment of Transurethral Laser Versus Transurethral Wicrowave Thermal Therapy*, Abstract: 12th World Congress on Endourology and SWL 8th Annual Frontiers in Endourology 10th Basic Research Symposium, Dec. 2–6, 1994, St. Louis, MO.

P. Miller et al., *Early Clinical Results Using the Urologix T3 Preferential Heating Transurethral Thermal Therapy Unit*, Abstrac: 12th World Congress on Endourology and SWL 8th Annual Frontiers in Endourology 10th Basic Research Symposium, Dec. 2–6, 1994, St. Louis, MO.

T. R. Larson et al., *Extent of Thermal Cell Death Correlated to Accurate Interstitial Temperatures of Ten Pathological Prostate Specimens Using Urologix T3 Microwave Transurethral Thermal Therapy Unit*, Abstract: 23rd Congress of Societe Internationale D'Urologie, Sep. 18–22, 1994, Sydney, Australia.

P.D. Miller et al., *Prostatic Thermal Ablation—The T3 System*, Abstract: 23rd Congress of Societe Internationale D'Urologie, Sep. 18–22, 1994, Sydney, Australia.

T.R. Larson et al., *Accurate Prostatic Thermal Mapping in 11 Patients Treated with the Urologix T3 System: Understanding the Decay of Temperatures*, Abstract: 23rd Congress of Societe Internationale D'Urologie, Sep. 18–22, 1994, Sydney, Australia.

T.R. Larson et al., *The Precipitous Fall of Intraprostatic Temperatures When Microwave Power is Stopped in Transurethral Thermal Therapy*, Abstract: 23rd Congress of Societe Internationale D'Urologie, Sep. 18–22, 1994, Sydney, Australia.

T.R. Larson et al., *Extent of Thermal Cell Death Correlated to Accurate Interstitial Temperatures of Ten Pathological Prostate Specimens Using Urologix T3 Microwave Transurethral Thermal Therapy Unit*, Abstract: 11th Congress of European Association of Urology, Jul. 13–16, 1994, Berlin, Germany.

P.D. Miller, *Prostatic Thermal Ablation—The T3 System*, Abstract: 11th Congress of European Association of Urology, Jul. 13–16, 1994, Berlin, Germany.

T.R. Larson et al., *Accurate Prostatic Thermal Mapping in 11 Patients Treated with the Urologix T3 System: Understanding the Decay of Temperatures*, Abstract: 14th Annual Meeting of North American Hyperthermia Society, Apr. 29–May 4, 1994. Nashville, Tennessee.

T.R. Larson et al., *The Role of Vasularity in Thermal Therapy: Use of Color Doppler During Urologic T3 Thermal Treatment of the Prostate*, Abstract: 14th Annual Meeting of North American Hyperthermia Society, Apr. 29–May 4, 1994, Nashville, Tennessee.

D.G. Bostwick et al., *Microwave Transurethral Thermal Therapy: Pathological Findings in the Canine Prostate*, Abstract: American Urological Association, May 15–20, 1993, San Antonio, Texas.

T.R. Larson et al., *Accurate Prostatic Thermal Mapping in 11 Patients Treated with the Urologix T3 System: Understanding the Decay of Temperatures*, Abstract: 11th World Congress on Endourology, Oct. 20–23, 1993, Florence, Italy.

T.R. Larson et al., *The Role of Vascularity in Thermal Therapy: Use of Color Doppler During Urologic T3 Thermal Treatmenet of the Prostate*, Abstract: Congreso Conjunto De Urologia, Sep. 4–9, 1992, Madrid, Spain.

Winston K. Mebust et al., *Prostatic Desiccation: A Preliminary Report of Laboratory and Clinical Experience*, The Journal of Urology, vol. 108, Oct. 1972, pp. 601–603.

M. Devonec et al., *Transurethral Microwave Thermotherapy (TUMT) in Patients with Benign Prostatic Hypertrophy*, Urology Departments Antiquaille Hospital, Claude Bernard University, LYON, France Charing Cross Hospital, LONDON, England.

S. Carter et al., *Objective Clinical Results of Transurethral Microwave Thermotherapy for Benign Prostatic Obstruction*, Urology Research Unit Charing Cross Hospital, Nov. 1990.

Marian Devonec et al., *Transurethral Microwave Heating of the Prostate–Or from Hyperthermia to Thermotherapy*, Journal of Endourology, vol. 5, No. 2, 1991, pp. 129–135.

Paul D. Miller et al., *Transurethral Microwave Thermo-Ablation (TUMT) for Benign Prostatic Hyperplasia Using a New Device (T3)*, American Urological Association, Apr. 23–28, 1995, Las Vegas, Nevada.

Devonec et al., *Transurethral Microwave Thermotherapy*, 1992 Monographs in Urology™, vol. 13, No. 4,.

Mendecki et al., *Microwave Applicators for Localized Hyperthermia Treatment of Cancer of the Prostate*, Int. Journal Radiation Oncology Biol. Phys. vol. 6, pp. 1583–1588.

P. Rigatti et al., *Local Deep Microwave Hyperthermia in the Treatment of Prostatic Diseases*, Arch. It. Urol. LXI: pp. 179–181, 1989.

Elizabeth F. Brown et al., *Proceedings of the DATTA Forum on Alternative Therapies for the Treatment of Benign Prostatic Hypertrophy*, American Medical Association, Nov. 12, 1991, pp. 1–28.

Rigatti et al., *Local Microwave Hyperthermia and Benign Prostatic Myperplasia Induced Bladder Outlet Obstruction*, Consensus on Hyperthermia for the 1990s, pp. 433–437, 1990.

M.A. Astrahan et al., *A Technique for Combining Microwave Hyperthermia with Intraluminal Brachytherapy of the Oesophagus*, Int. J. Hyperthermia, 1989, vol. 5, No. 1, pp. 37–51.

R.S. Kirby et al., *The Prostatron Transurethral Microwave Device in the Treatment of Bladder Outflow Obstruction due to Benign Prostatic Hyperplasia*, British Journal of Urology (1993), 72, pp. 190–194.

M. Devonec et al., *Transurethral Microwave Application: Temperature Sensation and Thermokinetics of the Human Prostate*, Abstract, Journal of Urology, vol. 143, No. 4, Apr. 1990, AVA 85th Annual Meeting May 13–17, 1990.

M. Devonec et al., *Review: Transurethral Microwave Thermotherapy in Benign Prostatic Hyperplasia*, Journal of Endourology, vol. 7, No. 3, 1993, pp. 255–259.

M. Devonec et al., *Thermoregulation during Transurethral Microwave Thermotherapy: Experimental and Clinical Fundamentals*, Eur Urol 1993, vol. 23 (suppl 1): pp. 63–67.

M. Devonec et al., *The Effects of Transurethral Microwave Thermotherapy (T.U.M.T.) in Patients with Benign Prostatic Hypertrophy*, Abstract, Eur Urol 1990, vol. 18, No. 1, p. 265.

M. Devonec et al., *Long Term Results of Transurethral Microwave Therapy (TUMT) in Patients with Benign Prostatic Hypertrophy*, Abstract, The Journal of Urology, vol. 145, No. 4, Apr. 1991, AUA Eighty–Sixth Annual Meeting Jun. 2–6, 1991.

M. Devonec et al., *Short and Long Term Histological Effects of Transurethral Microwave Therapy (TUMT) on Benign Prostatic Hypertrophy*, Abstract, The Journal of Urology, vol. 145, No. 4, Apr. 1991, AUA Eighty–Sixth Annual Meeting Jun. 2–6, 1991.

M. Devonec et al., *Microwave Thermotherapy in benign Prostatic Hypertrophy*, Current Opinion in Urology 1993, 3:202–208.

*Primary Examiner*—Jennifer Bahr
*Assistant Examiner*—Stephen Huang

[57] ABSTRACT

A method for treating an individual with diseased prostatic tissue, such as benign prostatic hyperplasia, includes inserting a catheter into a urethra to position a microwave antenna located within the catheter adjacent a prostatic region of the urethra. A microwave antenna is then driven within a power range for applying microwave energy substantially continuously to prostatic tissue to heat the prostatic tissue surrounding the microwave antenna at a temperature and for a time period sufficient to cause necrosis of the prostatic tissue.

36 Claims, 12 Drawing Sheets

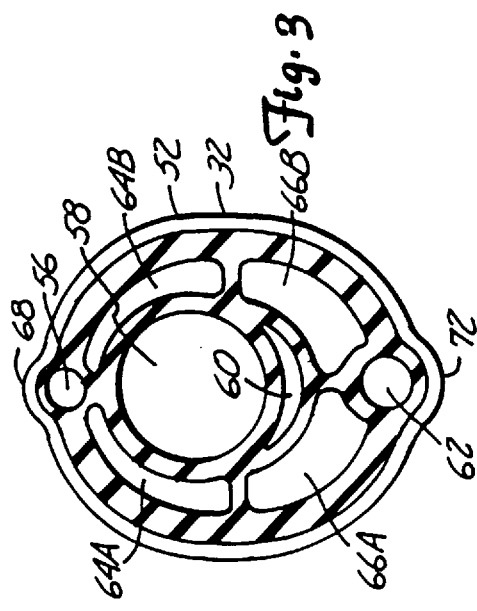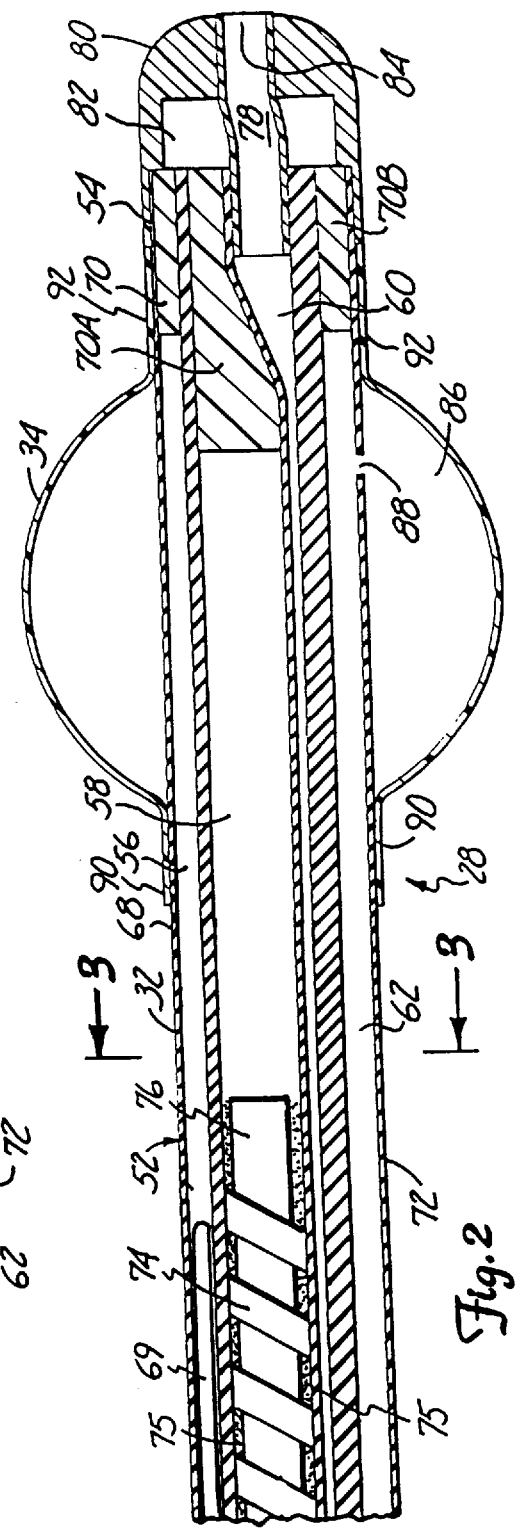

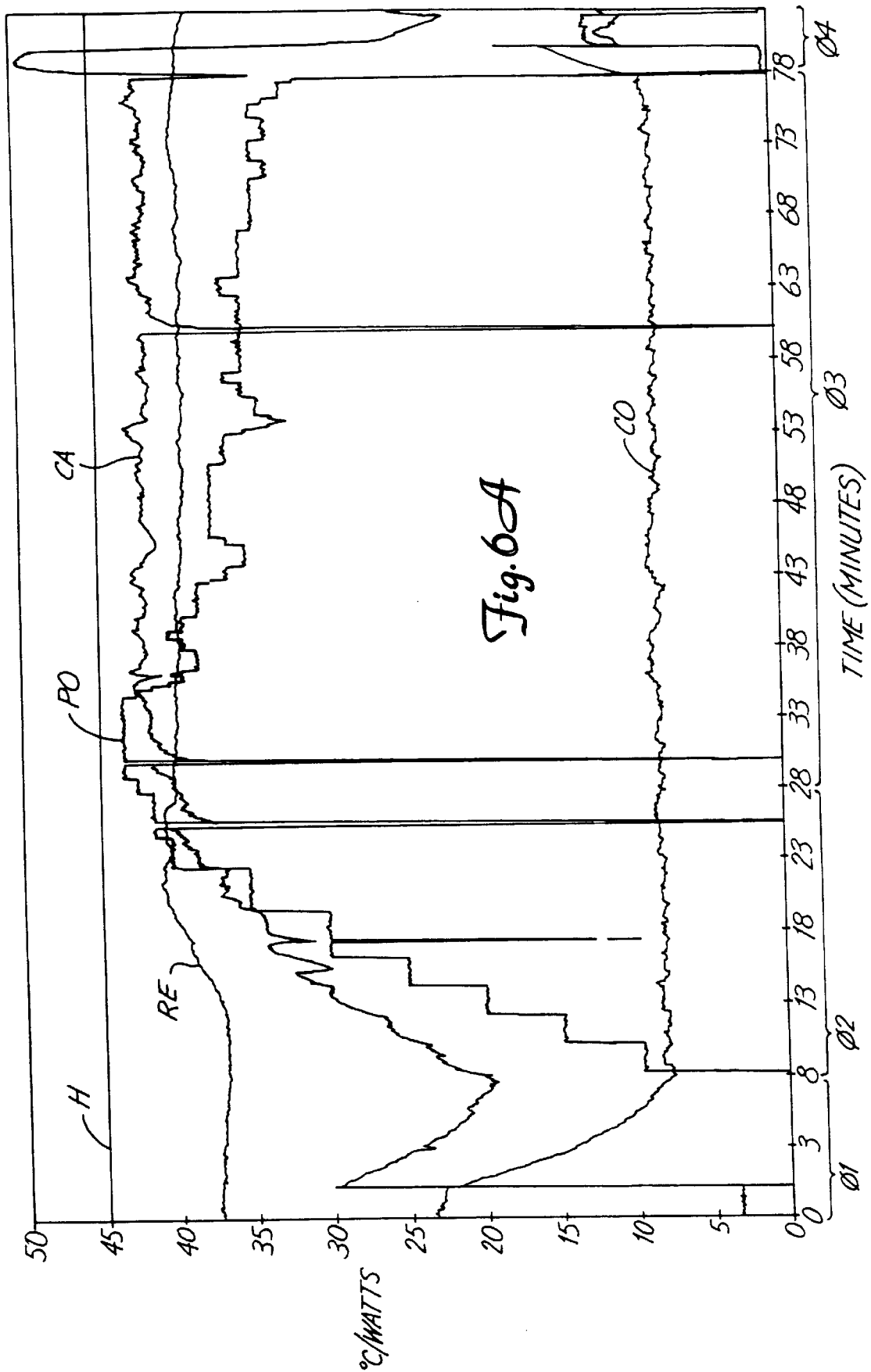

METHOD FOR TREATING BENIGN PROSTATIC HYPERPLASIA WITH THERMAL THERAPY

REFERENCE TO CO-PENDING APPLICATION

Reference is made to the following U.S. patent application: Ser. No. 08/309,137 filed Sep. 20, 1994, entitled METHOD FOR TREATING BENIGN PROSTATIC HYPERPLASIA WITH THERMAL THERAPY, by E. Rudie et al. Now U.S. Pat. No. 5,620,480.

BACKGROUND OF THE INVENTION

The present invention relates generally to the field of microwave thermal therapy of tissue. In particular, the present invention relates to a method for treating benign prostatic hyperplasia (BPH) and other prostatic tissue diseases with transurethral thermal ablation therapy.

The prostate gland is a complex, chestnut-shaped organ which encircles the urethra immediately below the bladder. This relatively small organ, which is the most frequently diseased of all internal organs, is the site of a common affliction among older men, benign prostatic hyperplasia (BPH), as well as a more serious affliction, cancer. BPH is a nonmalignant, bilateral nodular tumorous expansion of prostate tissue occurring mainly in the transition zone of the prostate. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

A fairly recent treatment method for BPH involves microwave thermal therapy, in which microwave energy is employed to elevate the temperature of tissue surrounding the prostatic urethra above about 45° C., thereby thermally damaging the tumorous BPH tissue. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation and generates a cylindrically symmetrical radiation pattern which encompasses and necroses the tumorous prostatic tissue. The necrosed intraprostatic tissue is subsequently reabsorbed by the body, thereby relieving an individual from the symptoms of BPH.

One type of thermal therapy treatment of BPH is transurethral microwave thermal therapy. This method of treatment positions a Foley-type catheter containing a microwave antenna within the urethra adjacent to the prostate gland to place the microwave antenna immediately adjacent the transition zone of the prostate. Intraurethral applicators of the type described can be found in Turner et al. U.S. Pat. No. 4,967,765 and Hascoet et al. European Patent Application 89403199.6.

However, a method of microwave thermal therapy based on the method and apparatus disclosed in Hascoet et al. European Patent Application 89403199.6 does not cause necrosis of the prostatic tissue at sufficient distances away from the urethra and with sufficient uniformity to necrose a complete volume of tumorous tissue typically present in the prostates of BPH patients. One reason for this poor performance resulting in shallow necrosis of the prostatic tissue surrounding the urethra is the method used to apply heat to the prostate. In particular, microwave energy is applied to the prostate at increasing power levels until a rectal temperature reaches 42.5° C. or the power applied is 60 watts. If the rectal temperature reaches 42.5° C., then microwave energy emission is completely stopped. Once the rectal temperature falls below 42° C., the application of microwave energy is resumed at a power level of five watts less than the power level applied before stopping the application of microwave energy. This method of applying microwave energy to the prostate is reported in Devonec et al., *Clinical Response to Transurethral Microwave Thermotherapy Is Thermal Dose Dependent,* 23 Journal of European Urology 267–274, 1993, and related papers by the same authors.

While the just described method causes some limited necrosis of prostatic tissue, the desired total volume of prostatic tissue is not necrosed at a sufficient depth or with sufficient uniformity to satisfactorily treat BPH. One problem with this method is that microwave power application is stopped for one to four minutes every time the rectal temperature exceeds 42.5° C. to wait for the rectal temperature to fall below 42° C. Each time this power interruption occurs, the intraprostatic temperatures generated by the transurethral catheter fall precipitously from a necrosing temperature level (from as high as 80° C.) down to a nonnecrosing level, about 40° C., within as little as two to three minutes. This phenomenon has been described in Larson et al., *The Precipitous Fall of Intraprostatic Temperatures When Microwave Power is Stopped in Transurethral Thermal Therapy,* 23rd Congress of Societe Internationale D'Urologie, Sydney, Australia, Sep. 18–22, 1994. This phenomenon was demonstrated by using a catheter (substantially corresponding to catheter 28 of the Rudie et al. U.S. Pat. No. 5,413,588) to produce both low level and high level (e.g., 80° C.) necrosing temperatures within intraprostatic tissue and then observing the amount of time required for the tissue temperature to fall to a nonnecrosing temperature (e.g., about 40° C.) upon discontinuing (i.e., completely stopping) the application of microwave energy to the intraprostatic tissue.

This phenomenon is believed to result from a hypervascularity response of the heated intraprostatic tissue. In particular, when the tissue is heated by applying microwave energy, blood vessels within the tissue dilate to carry more heat away via increased blood flow and increased blood volume. This dynamic vascular response is an attempt by the tissue to dissipate the heat being generated in the tissue by the microwave energy. However, within certain distances, the vascular system of the tissue is overwhelmed by the microwave energy and cannot dissipate heat fast enough to overcome the heat generated in the tissue. This situation remains unchanged as long as the application of microwave energy is maintained at sufficient levels in the tissue. However, when the application of microwave energy is substantially interrupted (e.g., stopped to allow rectal temperatures to fall), the microwave energy no longer overwhelms the ability of the vascular system to dissipate the heat within the tissue. Instead, in the absence of microwave energy, the heated tissue, in its hypervascular state, successfully acts as a heat sink to quickly dissipate the remaining heat in the tissue. This produces the rapid fall of intraprostatic tissue temperatures when the application of microwave energy is stopped.

Accordingly, substantial power interruptions in the application of microwave energy prevent the prostate from being heated continuously at necrosing temperatures during a one hour therapy session. Moreover, with each of these interruptions, more power and a longer period of time is required to reheat the prostatic tissue to a necrosing temperature, most likely because of the hypervascularity response by the tissue adjacent the microwave antenna. Accordingly, this prior art method results in much lower total application of necrosing heat to the prostate during a one hour therapy session due to frequent interruptions of the application of microwave energy, which also effectively makes the necrosing portion of therapy session less than one hour. Ultimately, a much lower total volume of prostatic tissue and a shallower depth of prostatic tissue is necrosed than desired. This results in fewer BPH patients treated with this prior art method having satisfactory outcomes.

SUMMARY OF THE INVENTION

The present invention is a method for treating an individual with prostatic tissue disease (e.g., benign prostatic hyperplasia) through the use of transurethral thermal ablation therapy. The present invention recognizes that effective treatment of BPH requires substantially continuous heating of prostatic tissue above at least 45° C. for a time sufficient to necrose the prostatic tissue. The method of the present invention can yield substantially uniform necrosis of the tissue of the prostate at a distance of at least two centimeters from the wall of the urethra.

A method of the present invention includes two main steps including inserting a catheter into a urethra and heating prostatic tissue while cooling the urethra. In particular, the method includes inserting a catheter into a urethra to position a microwave antenna located within the catheter adjacent a prostate surrounding the urethra. Tissue within the prostate is heated substantially continuously with microwave energy from the microwave antenna to temperatures of at least 45° C. at a distance of at least 2 centimeters from a wall of the urethra within the tissue while cooling the urethra.

The method of the present invention for treating an individual with prostatic tissue disease can further include the following steps. First, the urethra can be prechilled prior to heating tissue within the prostate. After pre-cooling the urethra, power is applied in increasing levels to the microwave antenna until predetermined criteria are met. The predetermined criteria are met when at least one of the following conditions exist: (1) the catheter temperature reaches a minimum temperature (e.g., 35° C.); (2) a temperature of the rectum reaches a minimum temperature (e.g., 40° C.); and (3) the power applied to the microwave antenna reaches a minimum power level (e.g., 35 Watts).

Next, power applied to the microwave antenna is maintained within a range which causes substantially continuous heating of tissue within the prostate to a temperature of at least 45° C. at a distance of at least 2 centimeters from the urethra while continuing to cool the urethra. The power level is maintained within a desired range which maintains a temperature of the rectum below 42° C. and the catheter temperature within 1° C. of 40° C. If the rectal temperature reaches 42° C., then the power level is decreased but not discontinued (i.e., completely stopped). In particular, the power level is decreased in increments of 1 watt per minute until the rectal temperature falls below 42° C. Then, the power level is increased in increments of one watt per minute until the catheter temperature is within 1° C. of 40° C. while still maintaining the rectal temperature below 42° C.

The method of the present invention permits the application of microwave energy at a power level and for a time sufficient to uniformly necrose tumorous prostatic tissue while preserving healthy tissue adjacent the prostate such as the urethra and the rectum. This technique applies power to the prostate to substantially continuously maintain intraprostatic temperatures within a therapeutic range at temperatures above at least 45° C. This method permits necrosing a larger total volume of tumorous prostatic tissue than possible with prior art methods since temperatures are maintained at necrosing levels substantially continuously throughout the therapeutic portion of the method of the present invention. With the method of the present invention, prostatic tissue can be necrosed at depths of at least 2 centimeters, which is generally sufficient to encompass a complete volume of BPH tumorous tissue within a prostate. Necrosing prostatic tissue at depths of 2 centimeters with the method of the present invention produces a post treatment result substantially similar to surgical treatment of BPH, in which prostatic tissue is removed at depths of about 2 centimeters. However, with the method of the present invention, the urethra can be preserved.

Moreover, the microwave energy can be applied in the method of the present invention in a preferential heating pattern to radiate more energy in the anterior and lateral portions of the prostate (where most BPH tumorous tissue is located) than in a posterior portion of the prostate. This also aids in preserving healthy tissue of the prostate as well as adjacent tissues such as the rectum.

BRIEF DESCRIPTION OF THE DRAWINGS

FIG. 2 is a sectional view of a proximal end of a urethral microwave thermal therapy catheter of Rudie et al., U.S. Pat. No. 5,413,588.

FIG. 3 is a sectional view of the catheter of FIG. 2 taken along lines 3—3.

FIG. 6A is a graph of measured temperature and microwave power supplied as a function of time illustrating a microwave thermal therapy procedure performed according to the method of the present invention.

DETAILED DESCRIPTION OF THE PREFERRED EMBODIMENTS

Figure 1:
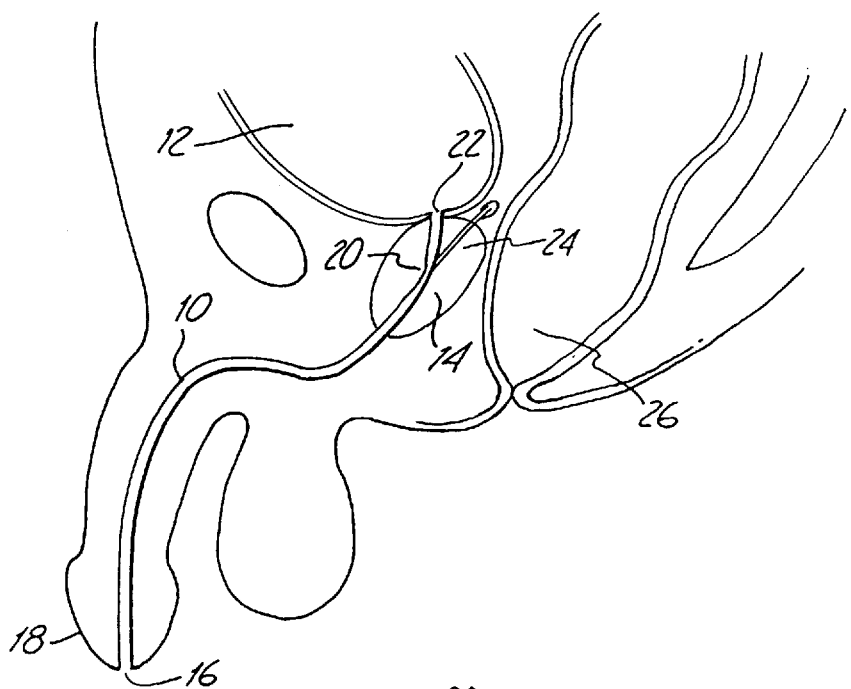
FIG. 1 is a vertical sectional view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26.

A. Catheter For Use in the Method of the Present Invention

Selective heating of the benign tumorous BPH tissue of prostate 14 according to the method of the present invention is possible using a microwave antenna-containing catheter 28 such as the one disclosed in Rudie et al. U.S. Pat. No. 5,413,588 on May 9, 1995 titled DEVICE FOR ASYMMETRICAL THERMAL THERAPY WITH HELICAL DIPOLE MICROWAVE ANTENNA and hereby incorporated by reference. While other urethral catheters can be used, catheter 28 of the Rudie et al. U.S. Pat. No. 5,413,588 is the preferred catheter for use in the method of the present invention. FIGS. 2 and 3 are provided to highlight the major features of catheter 28 of the Rudie et al. U.S. Pat. No. 5,413,588.

FIG. 2 shows an enlarged sectional view of a proximal end of catheter 28, which generally includes multi-lumen shaft 32 and shaft position retention balloon 34. At its distal end, the multi-lumen shaft 32 cooperates with a manifold for connecting multi-lumen shaft 32 with a cooling system, microwave generating source, and thermosensing device. Multi-lumen shaft 32 is a Foley-type urethral catheter shaft which is long enough to permit insertion of proximal shaft end 54 through urethra 10 and into bladder 12.

As shown in FIG. 3, multi-lumen shaft 32 of catheter 28 includes temperature sensing lumen 56, microwave antenna lumen 58, urine drainage lumen 60, balloon inflation lumen 62, cooling fluid intake lumens 64A and 64B, and cooling fluid exhaust lumens 66A and 66B.

Temperature sensing lumen 56 is positioned near first side 68 of shaft 32 and permits insertion of thermometry sensor 69 (FIG. 2) within shaft 32 to monitor the temperature of surrounding tissue when shaft 32 is inserted within urethra 10.

Microwave antenna lumen 58 is positioned closer to first side 68 of shaft 32 than to second side 72 of shaft 32. Microwave antenna 74 is permanently positioned within microwave antenna lumen 58 near balloon 34 to be generally situated adjacent the benign tumorous tissue of prostate 14 when shaft 32 is properly positioned within urethra 10. Antenna 74 can be energized by the microwave generating source thereby causing antenna 74 to emit electromagnetic energy which heats the tissue within prostate 14.

Urine drainage lumen 60 is positioned adjacent antenna lumen 58, between antenna lumen 58 and second side 72 of shaft 32, and defines a drainage path for urine when proximal end 54 of shaft 32 is inserted within bladder 12.

Balloon inflation lumen 62 communicates with an inflation port adjacent the distal end of the catheter 28 and with interior 86 of balloon 34. Balloon 34 is inflatable and deflatable and serves to retain shaft 32 in a fixed position when balloon 34 is inflated within bladder 12 near bladder neck 22, as shown in FIG. 4.

Cooling fluid intake lumens 64A, 64B are positioned circumjacent first side 68 of shaft 32, between first side 68 of shaft 32 and antenna lumen 58. Water contained within lumens 64A and 64B absorbs some of the microwave energy emitted by antenna 74. Water within lumens 64A and 64B also absorbs heat energy generated by the microwave energy from adjacent tissues to prevent urethra 10 adjacent first side 68 from being overheated and damaged when antenna 74 is energized.

Cooling fluid exhaust lumens 66A and 66B are circumjacent second side 72 of shaft 32. Water within exhaust lumens 66A, 66B also absorbs heat energy from adjacent tissue (i.e., urethra 10) when antenna 74 is energized, which prevents urethra 10 and rectum 26 adjacent second side 72 from being overheated and damaged when antenna 74 is energized.

Figure 4:
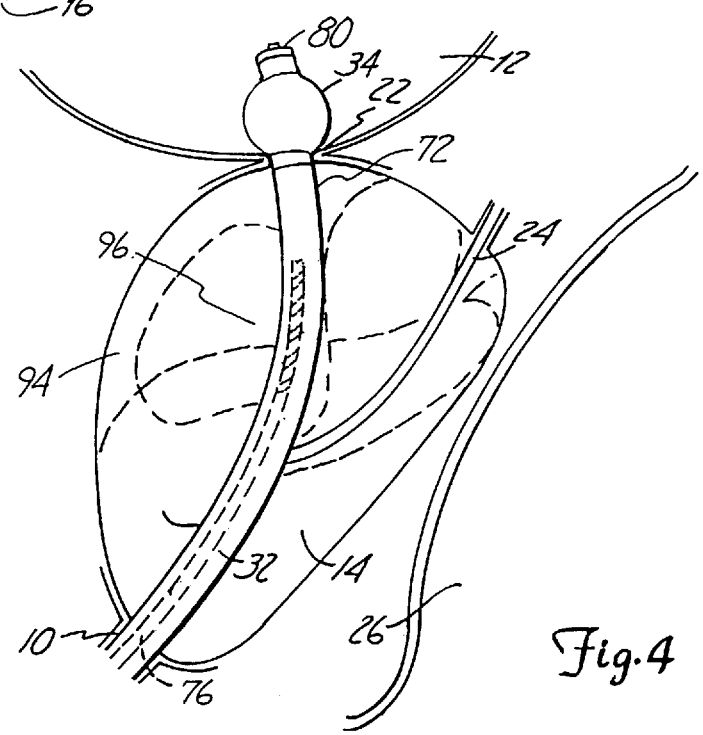
FIG. 4 is an enlarged view of the male pelvic region of FIG. 1 showing a urethral catheter of Rudie et al. U.S. Pat. No. 5,413,588 positioned within the prostate region.

FIG. 4 shows an enlarged view of the male pelvic region of FIG. 1 with catheter 28 properly positioned within urethra 10. Shaft 32 is positioned within urethra 10 with second side 72 of shaft 32 oriented toward rectum 26. Water exhaust lumens 66A and 66B are oriented posteriorly, toward rectum 26 and water intake lumens 64A and 64B are oriented anteriorly toward fibromuscular tissue 94 of prostate 14. The transition zone 96, which is typically anterior and lateral to urethra 10, is the most frequent location of the tumorous tissue growth which causes BPH. Since water exhaust lumens 66A and 66B are capable of absorbing more microwave energy than water intake lumens 64A and 64B, the radiation patterns created by microwave energy emitted from antenna 74 are asymmetrical. Thus, a relatively large volume of tissue enveloping the anterior portion of transition zone 96, adjacent first side 68 of shaft 32, is heated at a temperature above about 45° C., which effectively necroses the tumorous tissue of prostate 14 which encroaches upon urethra 10.

B. A Method for Treating Prostatic Tissue Disease

The method of transurethral thermal ablation therapy of the present invention includes the use of a microwave antenna containing catheter such as the just described catheter 28 of the Rudie et al Patent illustrated in FIGS. 2–4. A first step of the method includes inserting the urethral catheter into urethra 10 to position an energy producing source such as microwave antenna 74 within the catheter adjacent the prostate 14 surrounding urethra 10, as illustrated in FIG. 4.

Figure 5A:
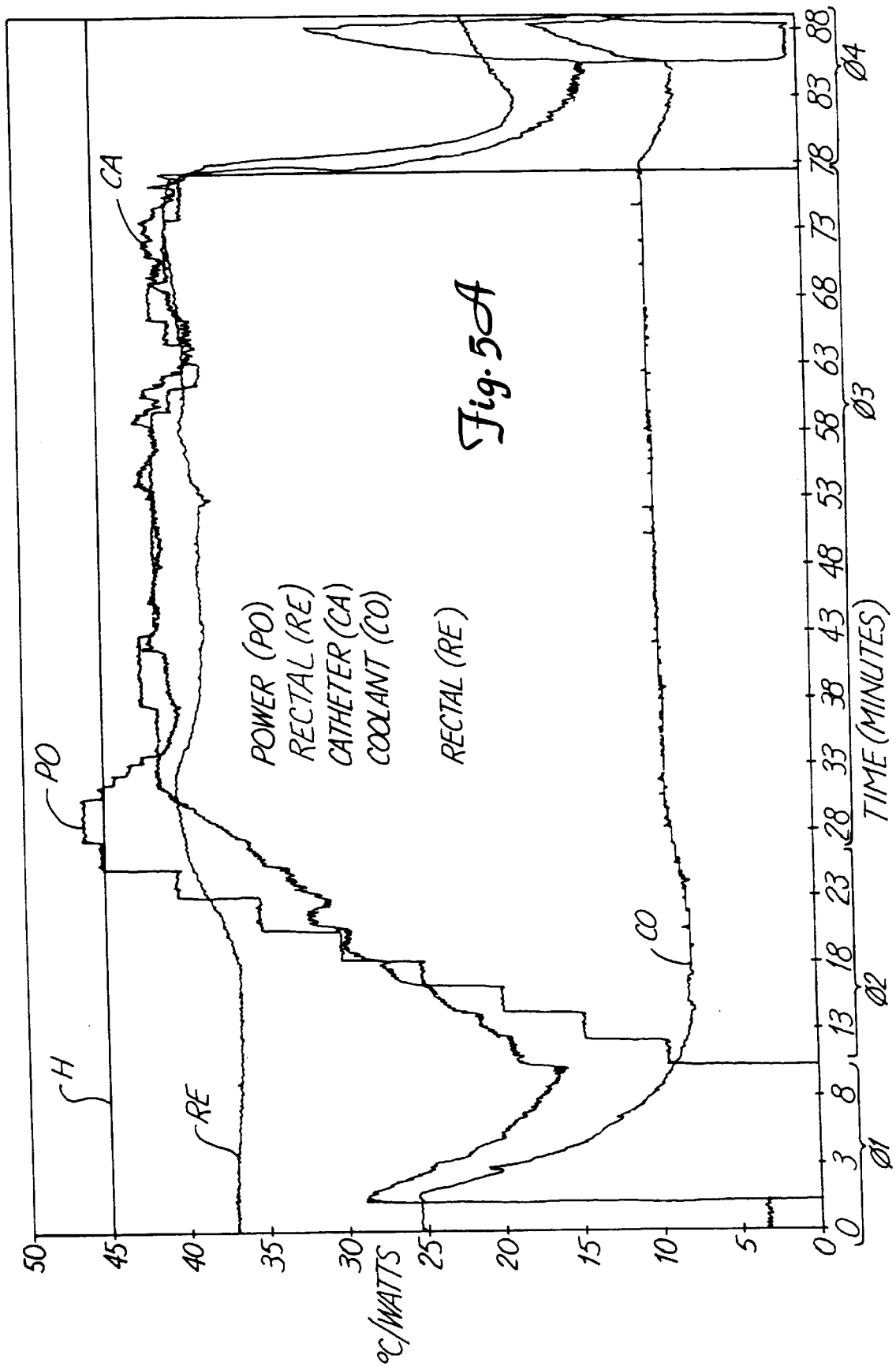
FIG. 5A is a graph of measured temperature and microwave power supplied as a function of time illustrating a microwave thermal therapy procedure performed according to the method of the present invention.

With the catheter positioned within the urethra, a transurethral thermal ablation therapy procedure of the method of the present invention can begin. FIG. 5A is a graph which generally demonstrates a transurethral thermal ablation therapy procedure substantially corresponding to the method of the present invention. However, the method of the present invention is not limited to the exact procedure shown in FIG. 5A (or FIG. 6A). Rather, the procedure shown in FIG. 5A is merely an example of an application of the method of the present invention and is being used for illustrative purposes to describe the method of the present invention.

As shown in FIG. 5A, the x-axis represents a relative period of time over which the transurethral thermal ablation therapy procedure is performed. The y-axis represents temperature in degrees Celsius, with horizontal line H representing 45° C. (the temperature at or above which cells are necrosed), and power expressed in Watts. Line PO represents power applied to microwave antenna 74 (via coaxial cable 76), line CA represents a temperature of the catheter measured by sensor 69, line CO represents a temperature of the coolant within catheter 28, and line RE represents a temperature of the rectum as measured by a rectal thermosensing unit. The power PO applied to microwave antenna 74 (at a proximal-most end of coaxial cable 76) is measured at a distalmost end of coaxial cable 76 of microwave antenna 74 adjacent fitting 73 (see FIG. 2A of the Rudie et al U.S. Pat. No. 5,326,343).

As generally shown in FIG. 5A, the transurethral thermal ablation therapy procedure of the present invention includes four operating phases, Φ1–Φ4. These phases include a first cooling phase Φ1, a second power ramping phase Φ2, a third power maintenance phase Φ3, and a fourth power shutdown/cooling phase Φ4.

During first phase Φ1, the urethra is cooled to a temperature below human body temperature by circulating coolant fluid within the catheter between the microwave antenna and the urethra. This cooling step includes using a cooling system in communication with catheter 28 to pump chilled water through cooling lumens 64A, 64B and 66A, 66B until the temperature of the coolant within lumens 64A, 64B and 66A, 66B is less than or equal to 10° C. Line CO of the graph illustrates the drop in temperature of the coolant in phase Φ1 and line CA illustrates the corresponding drop in the temperature of the catheter (sensor 69 of catheter 28) in phase Φ1. First phase Φ1 results in a prechilling of the tissue immediately adjacent shaft 32 to prevent urethra 10 from being damaged by heat due to the relatively rapid application of power to microwave antenna 74 in the second phase Φ2 of the method. Cooling of the urethra with the catheter is maintained throughout the remaining steps of the method of the present invention. However, if desired, the prechilling of urethra 10 in first phase Φ1 can be omitted prior to the application of later steps of the method.

A second phase Φ2 of the method of the present invention is a power ramping phase in which power is increasingly applied to microwave antenna 74 until predetermined criteria are met. Line PO of the graph in FIG. 5A illustrates the application of increasing power levels to microwave antenna 74. Applying power to microwave antenna 74 causes a microwave emission to be applied to the tissue of the prostate 14 thereby causing molecular excitation of the tissue. When the power level applied to microwave antenna becomes great enough to heat the tissue to at least 45° C., and is applied for a sufficient period of time, this microwave emission will cause necrosis of the tissue within a distance affected by the microwave emission. In addition, when a catheter such as catheter 28 is used in the method of the present invention, a cylindrically asymmetrical microwave radiation pattern is applied to the prostate by microwave emission to preferentially heat a greater amount of tissue in the anterior and lateral portions of the prostate than a posterior portion of the prostate.

In a first portion of power ramping phase Φ2, 10 watts of power at frequencies between 902 and 928 MHz is applied to microwave antenna 74 for about two minutes. Next, in a second portion of second phase Φ2, the power applied to microwave antenna 74 is increased in 5 Watt increments at two minute intervals until a first predetermined criteria is met. Finally, in a third portion of power ramping phase Φ2, the power applied to microwave antenna 74 is further increased in one watt increments at one minute intervals until a second predetermined criteria is met.

The first predetermined criteria can include that at least one or more of the three following conditions exist: (1) the catheter temperature (i.e., thermal catheter sensor 69 within temperature sensing lumen 56) reaches a minimum temperature (e.g., 35° C.); (2) power applied to microwave antenna 74 reaches a minimum level (e.g., 35 Watts); or (3) the rectal temperature as measured by a rectal temperature sensing unit (RTU) reaches a minimum temperature (e.g 40° C.). The second predetermined criteria is that the catheter temperature is within 1° C. of 40° C. Once the second predetermined criteria is met, the second phase of the method of the present invention is complete. Of course, if the second predetermined criteria is met after the application of power (in five watt increments) in the second portion of second phase Φ2, then further increases of power in one watt increments in the third portion of the second phase need not be applied.

Once the catheter temperature reaches 37° C. during second phase Φ2, this point marks the beginning of therapeutically effective portion of the method of the present invention. Typically, the therapeutic portion of the procedure begins at the later stages of the second phase shortly after the first predetermined criteria have been met.

In the specific procedure shown in FIG. 5A, the second phase of the method began at 10 minutes and ended at 27 minutes into the procedure. Power was increased in five watt increments several times between 12 minutes and 24 minutes of the procedure. This increasing application of power to the microwave antenna resulted in a corresponding increase in the catheter temperature illustrated by line CA. The therapeutic portion of this procedure began at about 27 minutes into the procedure when the catheter temperature reached about 37° C. At that point in the procedure, the power was increased only one time in a one watt increment since the catheter temperature was already rapidly rising and quickly reached 40° C. without a further increase in power. Accordingly, the second phase Φ2 shown in FIG. 5A did not include an extended third portion of second phase Φ2 in which the power was increased several times in one watt increments after the first predetermined criteria were met.

The third phase of the method of the present invention includes maintaining the power level within a desired power range to maintain a catheter temperature within 1° C. of 40° C. to cause heating of prostatic tissue at temperature of at least 45° C. Power levels applied to antenna 74 are adjusted, either up or down, in one watt increments every minute as necessary to maintain a continuous application of heat at necrosing temperatures (i.e., 45° C.) to the prostatic tissue at distances of at least 2 centimeters from wall of the urethra.

The third phase of the method of the present invention also includes maintaining the temperature of the rectum 26 adjacent the prostate 14 below 42° C. If during third phase Φ3, the rectal temperature reaches 42° C., then the power applied to microwave antenna 74 is not completely stopped but decreased at one minute intervals in one watt increments until the rectal temperature moves below 42° C. Once the rectal temperature is below 42° C., then the power applied to microwave antenna 74 is increased in one watt increments as necessary to maintain the temperature of the catheter (sensor 69) within 1° C. of 40° C. while still maintaining the rectal temperature below 42° C.

In the specific procedure shown in FIG. 5A, phase Φ3 lasted about 50 minutes (i.e., 27 to 78 minutes along x-axis). First, the power reached a peak of about 46–47 watts at the end of second phase Φ2. The power was then adjusted according to the method of the present invention by decreasing the power in one watt increments five times at about one minute intervals (see 30–35 minutes on x-axis) in order to counteract a rapidly rising catheter temperature. Thereafter, the power applied to microwave antenna 74 was adjusted periodically to maintain the catheter temperature within 1°

C. of 40° C. This continuous application of power to antenna 74 resulted in maintaining intraprostatic temperatures of at least 45° C. at distances of at least 2 centimeters from the wall of the urethra (shown in FIGS. 5B–5D). As shown in FIG. 5A, despite the continuous application of power at necrosing levels to the microwave antenna 74, the rectal temperature (illustrated by line RE) only briefly rose above 40° C. during this application of the method of the present invention.

While the third phase Φ3 of the procedure shown in FIG. 5A lasted about 50 minutes, the method of the present invention is not limited to an application of microwave energy of 45 to 50 minutes. Rather, the present invention is based on the recognition that necrosis of prostatic tissues depends on a time and temperature relationship. Accordingly, if relatively higher temperatures (e.g., 80° C.) can be produced in the intraprostatic tissue, then the time period for which microwave energy is applied can likely be reduced to a time period less than 45 to 50 minutes while still successfully achieving uniform, deep necrosis of diseased prostatic tissue and preserving the urethra.

The fourth phase Φ4 of the method of the present invention is a power shutdown/cooling phase. In this phase, the power applied to microwave antenna 74 is discontinued and cooling of the urethra is maintained after discontinuing power. In particular, power applied to microwave antenna 74 is reduced to zero watts and coolant flow through cooling lumens 64A,64B and 66A,66B is maintained at 8° C. for about ten minutes (following the power level reaching zero watts) to cool urethra 10 and reduce edema resulting from the application of heat to the periurethral tissues of prostate 14.

In the specific procedure shown in FIG. 5A, fourth phase began after about 50 minutes of the therapeutic portion of third phase Φ3. During fourth phase Φ4, the catheter temperature (line CA) dropped immediately from about 40° C. to a temperature below 15° C. thereby cooling urethra 10 about catheter shaft 32. Likewise, during fourth phase Φ4, the rectal temperature (line RE) dropped from about 38° C. to about 18° C., thereby cooling the rectum 26 after third phase Φ3. This cooling step completes the fourth phase and the method of the present invention.

C. The Method of the Present Invention as Applied to BPH Patients

The method of the present invention using catheter 28 was employed in a study in Mendoza, Argentina in December 1993 on 10 patients according to a protocol established by the assignee of the present application, Urologix, Inc, of Plymouth, Minn. Further details about the study are available from Urologix, Inc. A temperature distribution profile and histological report for two patients from that study is provided below. This information demonstrates the effectiveness of treating BPH with the method of the present invention, and in particular demonstrates the ability of the method to produce necrosing intraprostatic temperatures of at least 45° C. at distances of at least 2 centimeters from the urethra (e.g., the wall of the urethra in contact with catheter shaft 32). This information also demonstrates the ability of the method to produce uniform necrosis within the prostate at distances of at least 1.8 centimeters from the wall of the urethra.

1. A Temperature Profile of Prostate Tissue Treated According to the Method of the Present Invention FIGS. 5A–5D and 6A–6D are a series of graphs which generally demonstrate a transurethral thermal ablation therapy procedure and a temperature distribution generated by catheter 28 of the Rudie et al. U.S. Pat. No. 5,413,588 within prostate 10 according to a method of the present invention. FIGS. 5A–5D correspond to the treatment of a first patient (Patient 30 of the study) and FIGS. 6A–6D correspond to the treatment of a second patient (Patient 35 of the study).

a. FIGS. 5A–5D—Patient 30

Figure 5B:
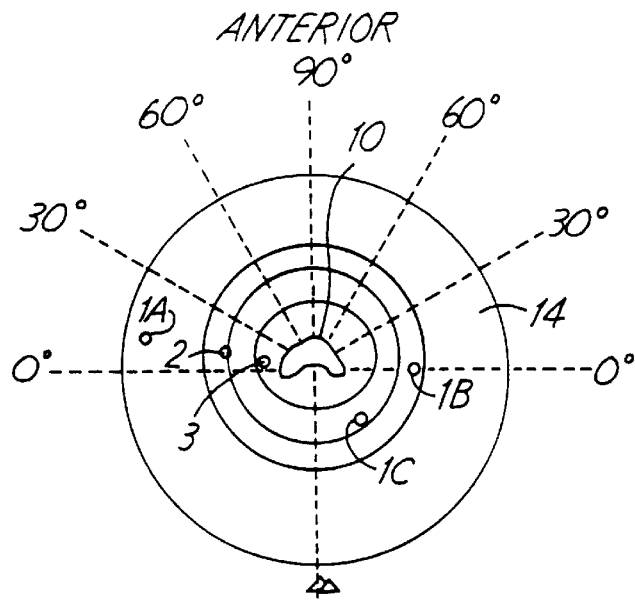
FIG. 5B is a map illustrating the location of temperature sensors placed within the prostate of a patient during the microwave thermal therapy procedure shown in FIG. 5A.
Figure 5C:
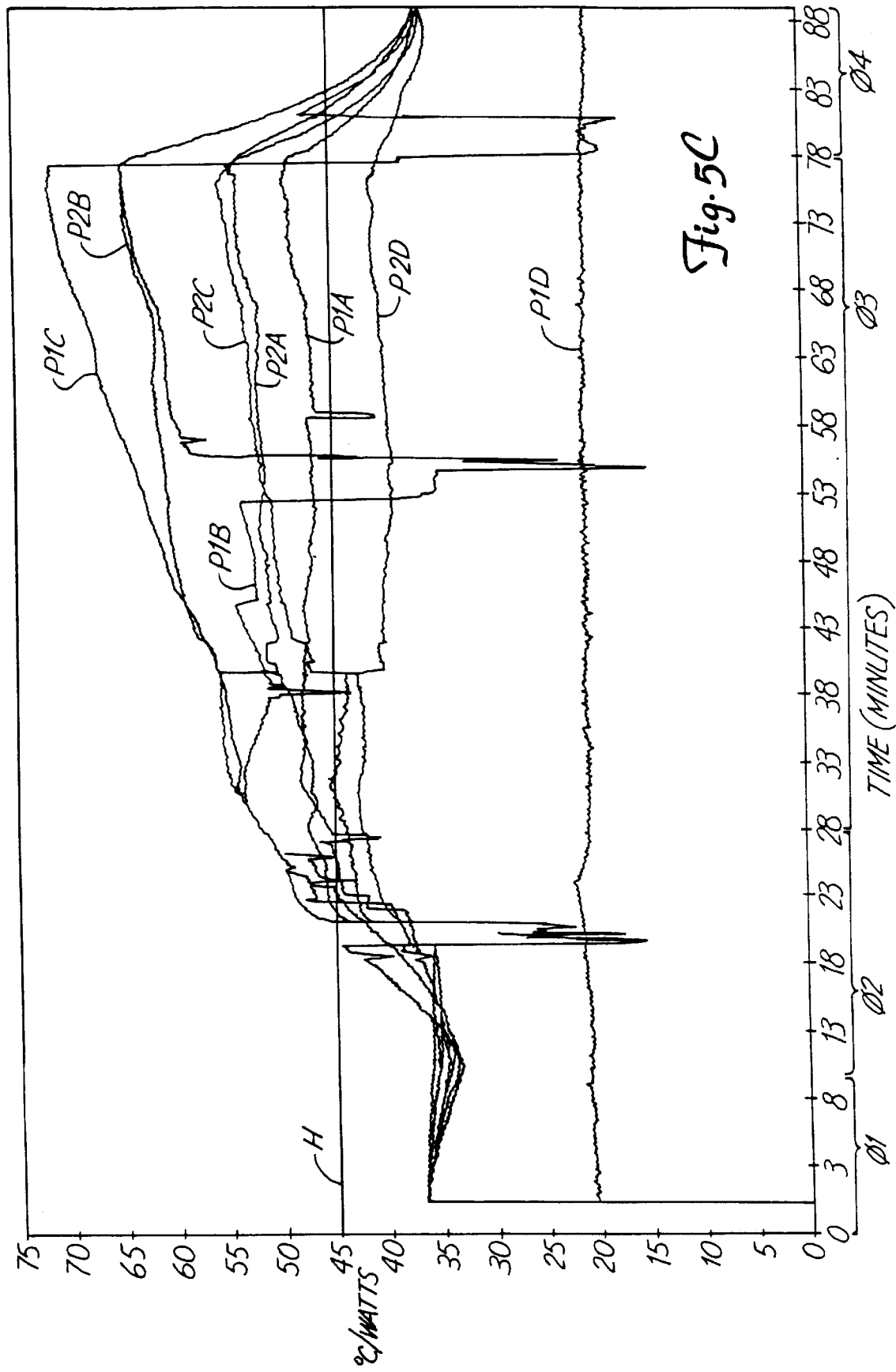
FIGS. 5C–5D are graphs illustrating a temperature distribution, as a function of time, generated by a urethral catheter in the method of the present invention.
Figure 5D:
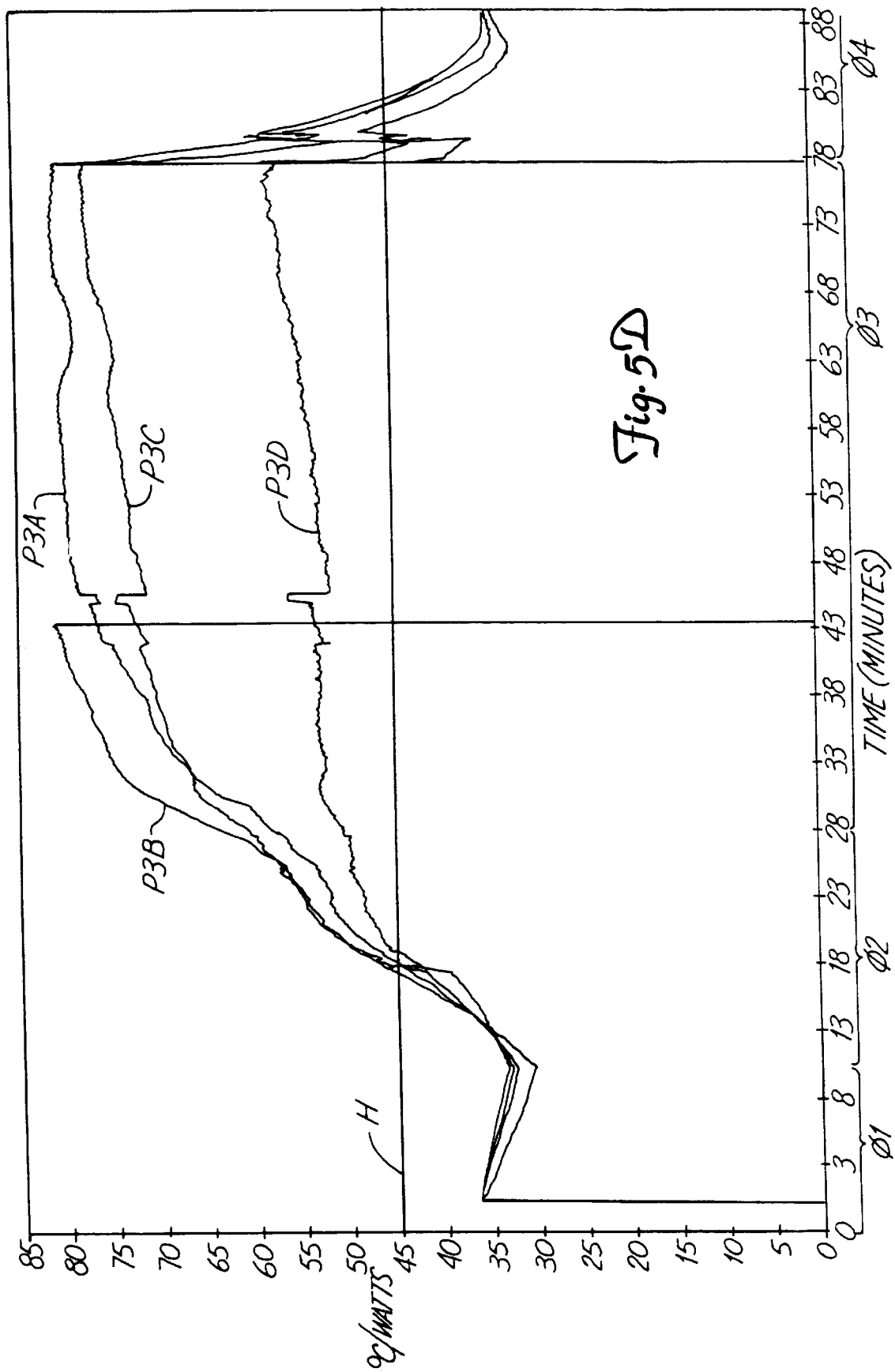

FIGS. 5C–5D illustrate a temperature distribution, as a function of time, in a prostate of Patient 30. This temperature distribution was generated by the use of catheter 28 in the previously described transurethral thermal ablation therapy procedure of the method of the present invention illustrated in FIG. 5A.

FIG. 5B illustrates a map identifying the location of temperature sensors located within the prostate of Patient 30 during treatment by the method of the present invention. The sensors were placed according to an interstitial mapping method substantially corresponding to the method referenced in Larson et al., *Accurate Prostatic Thermal Mapping in* 11 *Patients Treated With The Urologix T3 System: Understanding the Decay of Temperatures,* 11th World Congress on Endourology, Florence, Italy, Oct. 20–23, 1993.

Eleven sensors were aligned at fixed distances adjacent urethra 10. Sensor P1A was positioned about 20 mm from shaft 32, laterally and slightly anterior to shaft 32; sensor P1B was positioned about 9 mm from shaft 32 laterally from shaft 32 on a side of the prostate opposite sensor P1A; sensor P1C was positioned about 7 mm from urethra 10, posteriorly of the urethra 10; and sensor P1D was not in use (FIG. 5C). Sensors P2A–P2D were positioned about 13 mm from shaft 32, lateral to urethra 10 and spaced longitudinally from each other by 1 cm to extend substantially vertically within the prostate along a length of the microwave antenna. Sensors P3A–P3D were positioned about 8 mm from shaft 32, lateral to urethra 10 and spaced longitudinally from each other by 0.5 cm to extend substantially vertically within the prostate along a length of the microwave antenna.

FIG. 5C illustrates temperatures measured within the prostate of Patient 30 by sensors P1A–P1C and P2A–P2D. At the beginning of the therapeutic portion of the procedure (about 27 minutes on x-axis), sensors P1A–P1C and P2A–P2D measured intraprostatic temperatures above 45° C., which were maintained through the end of third phase Φ3. In particular, sensor P1A which was positioned 20 mm from the urethra, measured a temperature of over 45° C. substantially continuously for the length of the therapeutic session, about at least 45 minutes.

FIG. 5D illustrates temperatures measured within the prostate of Patient 30 by sensors P3A–P3D. The beginning of the therapeutic portion of the procedure (about 27 minutes on x-axis), sensors P3A–P3D measured intraprostatic temperatures about 45° C. which were maintained through the end of the third phase Φ3. Sensors P3A and P3C measured temperatures of near 80° C. which were maintained for up to 30 minutes during the therapeutic portion of the method in third phase Φ3. Sensor P3B reached a temperature of over 80° C. about 43 minutes into the procedure, resulting a display default of 0° C. due to a limitation of the data display software.

b. FIGS. 6A–6D—Patient 35

Figure 6B:
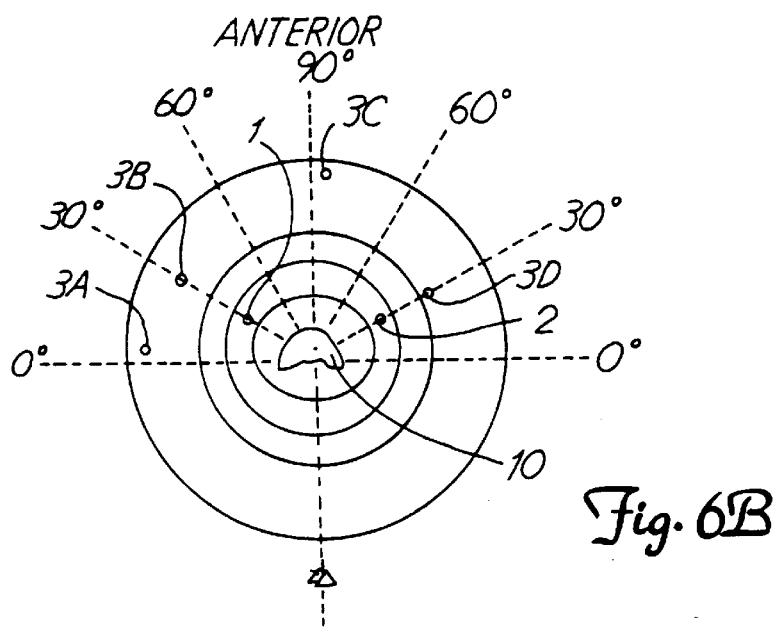
FIG. 6B is a map illustrating the location of temperature sensors placed within the prostate of a patient during the microwave thermal therapy procedure shown in FIG. 6A.
Figure 6C:
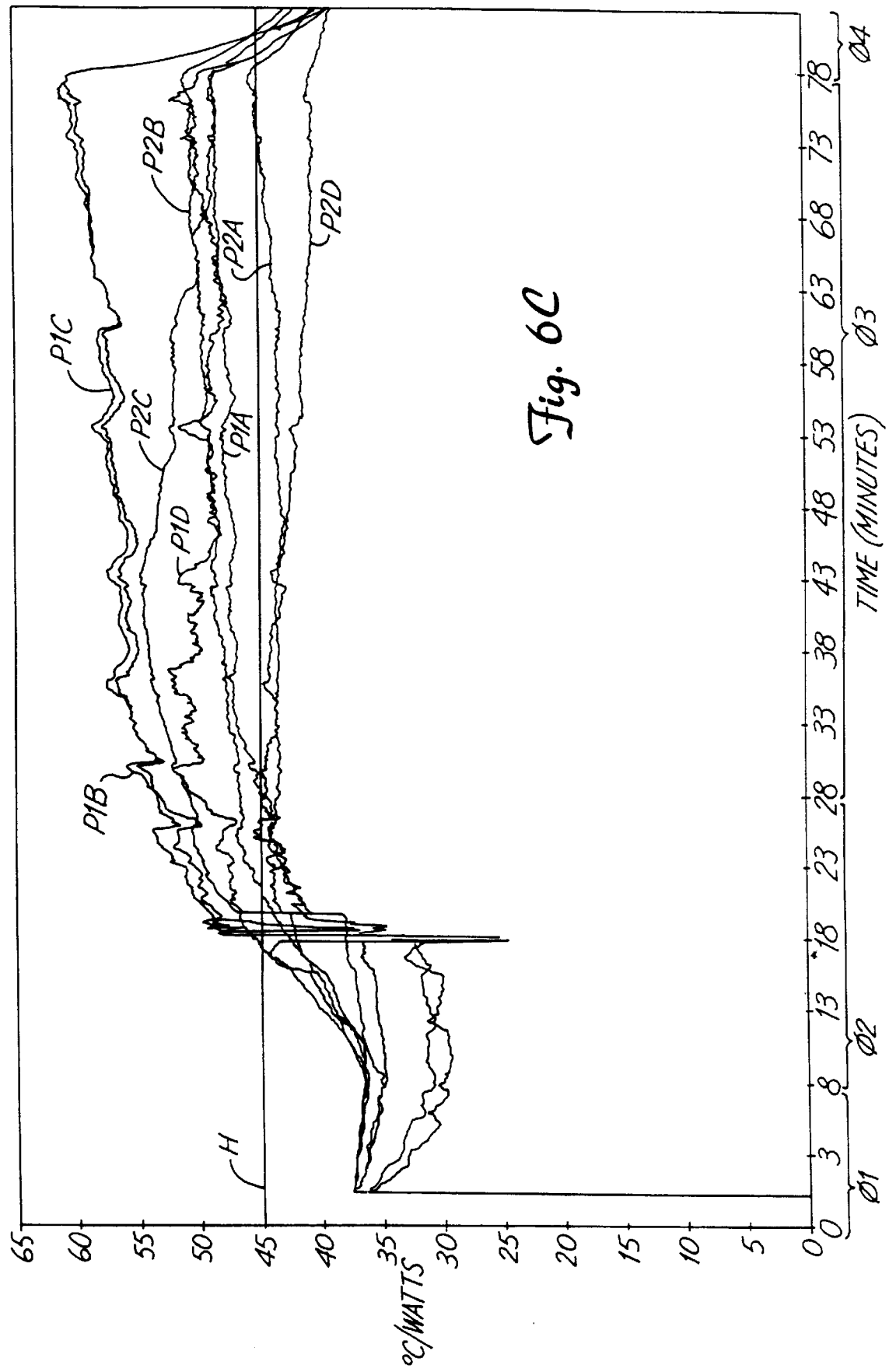
FIGS. 6C–6D are graphs illustrating a temperature distribution, as a function of time, generated by a urethral catheter in the method of the present invention.
Figure 6D:
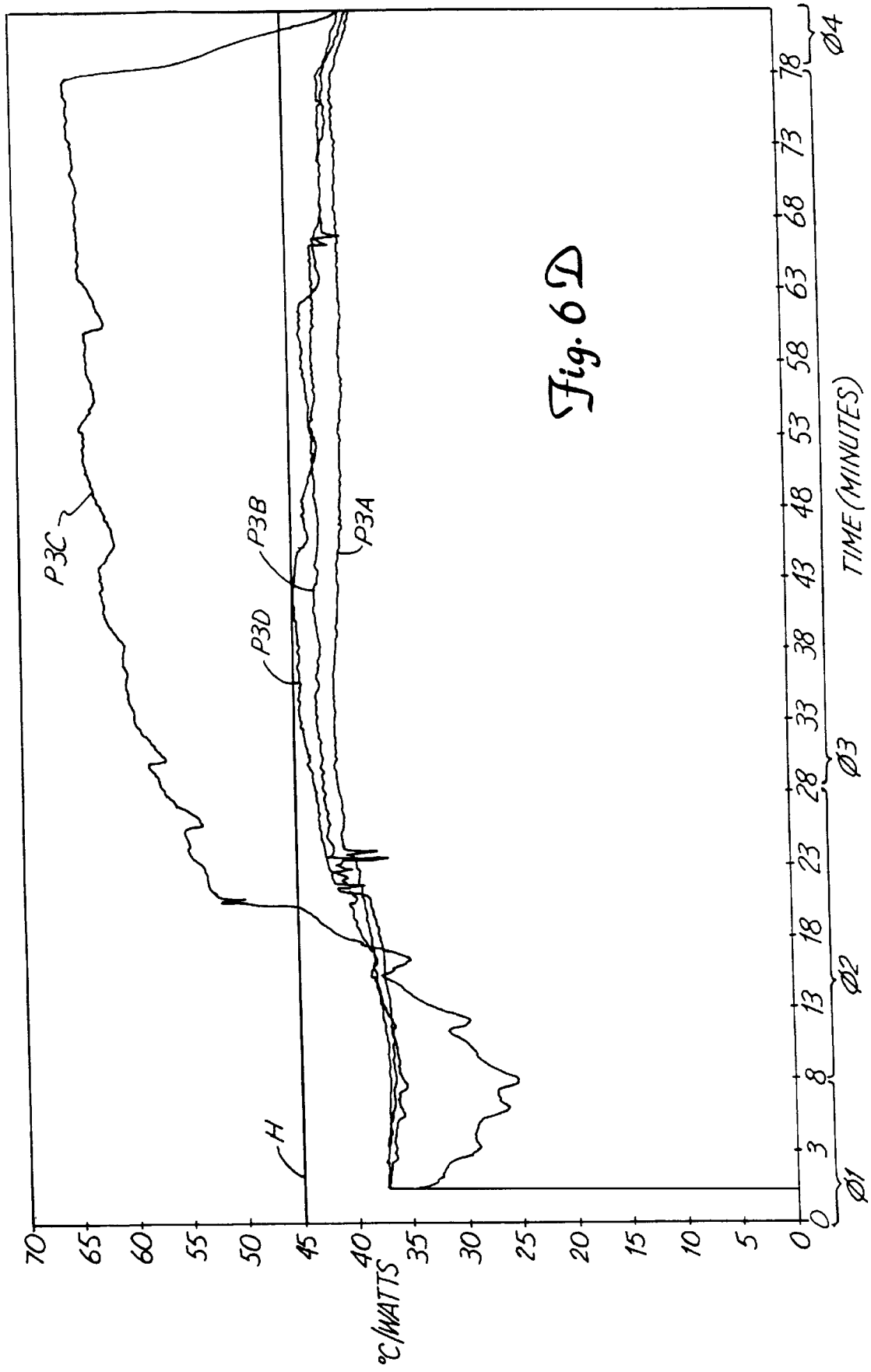
Figure 7A:
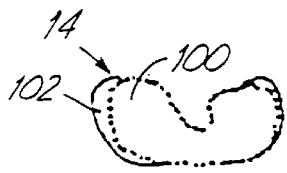
FIGS. 7A–7J are a pictorial representation of a series of cross sections of a prostate of a first patient treated according to the method of the present invention.
Figure 7F:
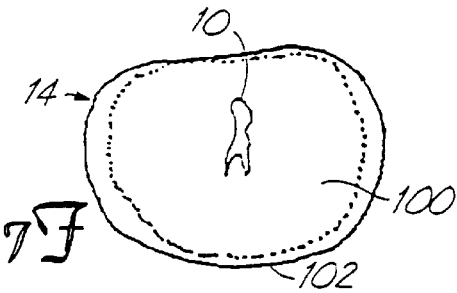
Figure 7B:
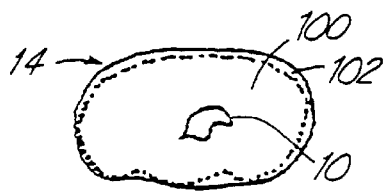
Figure 7G:
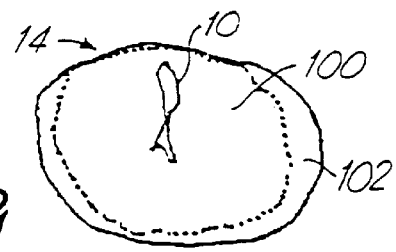
Figure 7C:
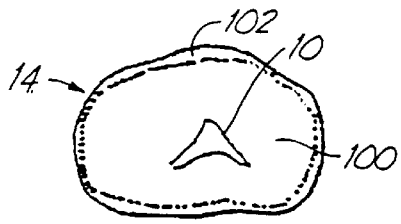
Figure 7H:
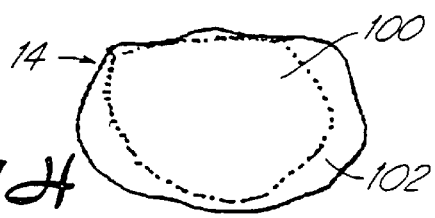
Figure 7D:
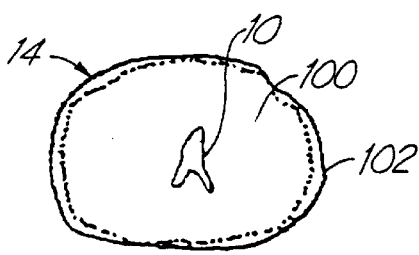
Figure 7I:
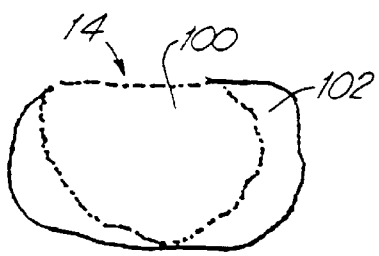
Figure 7E:
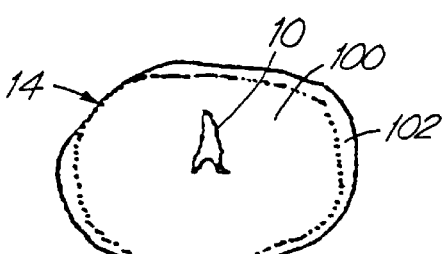
Figure 7J:
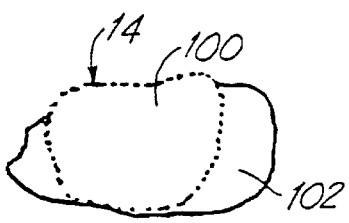

FIGS. 6C–6D illustrate a temperature distribution, as a function of time, in a prostate of Patient 35. This temperature distribution was generated by the use of catheter 28 in a transurethral thermal ablation therapy procedure of the method of the present invention illustrated in FIG. 6A.

FIG. 6A illustrates a microwave thermal therapy procedure of the present invention similar to that previously described with respect to FIG. 5A. First phase Φ1 begins at 1 minute and extends until about 8 minutes. Second phase Φ1 extends from 8 minutes into the procedure to about 28 minutes, at which time, the catheter temperature (line CA) reaches about 40° C. Third phase Φ3 extends from about 28 minutes to about 78 minutes along x-axis. The therapeutic portion of the method begins about 20 minutes into the procedure at which time the catheter temperature is about 37° C. Beginning at about 28 minutes into the procedure, the catheter temperature (line CA) is maintained at or slightly above 40° C. through the end of phase Φ3.

FIG. 6B illustrates a map identifying the location of temperature sensors located within the prostate of Patient 35 during treatment by the method of the present invention. Multiple sensors were aligned at fixed distances adjacent urethra 10. Sensors P1A–P1D were positioned about 6 mm from shaft 32, lateral and anterior to urethra 10 and spaced longitudinally from each other by 1.0 cm to extend within the prostate along a length of the microwave antenna; sensors P2A–P2D were positioned about 12 mm from shaft 32, lateral and anterior to urethra 10 on a side of the prostate opposite the sensors P1A–P1D and spaced longitudinally from each other by 1.0 cm to extend within the prostate along a length of the microwave antenna; sensor P3A was positioned about 18 mm from shaft 32 on a right side of the patient lateral to and slightly anterior of urethra 10; sensor P3B was positioned about 15 mm from shaft 32 lateral to an anterior of urethra 10, being more anterior relative to sensor P3A; sensor P3C was positioned about 20 mm from shaft 32 directly anterior from urethra 10; sensor P3D was positioned about 18 mm from shaft 32 lateral to and slightly anterior of urethra 10 on a side of the prostate opposite sensors P3A and P3B.

FIG. 6C illustrates temperatures measured within the prostate of patient 35 by sensors P1A–P2D. FIG. 6C illustrates that almost all of the sensors P1A–P2D, except sensors P2A and P2D measured intraprostatic temperatures above 45° C. which were maintained through the end of third phase Φ3. At the beginning of the therapeutic portion of the procedure (about 20 minutes on x-axis), sensors P1A–P1D and P2B,P2C measured a temperature within the prostate of over 45° C. which was maintained throughout the duration of the therapeutic portion of the procedure (through 78 minutes).

FIG. 6D illustrates temperatures measured within the prostate of Patient 35 by sensors P3A–P3D. At the beginning of the therapeutic portion of the procedure (about 20 minutes on x-axis), sensor P3C measured intraprostatic temperatures above 45° C. (at least 50° C.) which were maintained through the end of the third phase Φ3, lasting the duration of the therapeutic portion of the procedure (through 78 minutes). A peak temperature of about 65° C. was measured by sensor P3C. However, temperatures measured by sensors P3A,P3B and P3D never rose above 45° C. during the third phase Φ3.

d. Summary

FIGS. 5A–5D and 6A–6D illustrate that the method of the present invention, which includes the continuous application of power to a microwave antenna within a desired range to maintain the catheter temperature 1° C. within 40° C. and a rectal temperature below 42° C., results in intraprostatic temperatures of at least 45° C. continuously for over 45 minutes at distances of up to 2 centimeters from the urethra.

Moreover, FIGS. 5A, 5C–5D highlight the unique features of transurethral thermal ablation therapy of the method of the present invention. In transurethral thermal ablation therapy, prostatic tissues can be simultaneously heated to high necrosing temperatures (up to 80° C.) at distances (e.g., about 0.8 centimeters) relatively close to the wall of the urethra (see FIG. 5D illustrating temperatures at sensor P3A–P3D) while preserving the urethra, and heated to lower necrosing temperatures of at least 45° C. at distances of at least 2 centimeters from the wall of the urethra (see FIG. 5C illustrating temperatures at sensor P1A). Producing temperatures as high as 80° C. within the prostate relatively close to the urethra (while preserving the urethra) is an important factor in achieving necrosing temperatures at distances of up to and/or at least 2 centimeters from the urethra in light of the well established exponential decay of elevated intraprostatic temperatures (generated by microwave energy) outwardly throughout the prostate relative to the urethra.

A significant factor in achieving transurethral thermal ablation therapy instead of achieving conventional microwave thermal therapy is maintaining continuous application of microwave energy (i.e., without substantial interruption), for a sufficient time period and in a power range to continuously maintain necrosing temperatures at desired distances. Without maintaining a substantially continuous application of microwave energy (by continuous application of power to the microwave antenna), a transurethral thermal ablation therapy temperature profile in intraprostatic tissue cannot be achieved (using microwave energy applied by a microwave antenna located within the urethra).

2. Pathology Reports

FIGS. 7A–8I represent a series of cross-sections of prostates harvested from Patients 30 and 35 of the study to illustrate the relative degree of necrosis of the prostate after treatment according to a method of the present invention.

a. Patient 30

FIGS. 7A–7J illustrate a series of sketches of cross-sections of a prostate harvested from Patient 30 by prostatoseminovesiculectomy some time after treatment under the method of the present invention (illustrated by the procedure in FIG. 5A). The pathologic report on this prostate was rendered by David Bostwick, M.D. of Mayo Clinic in Rochester, Minn. This pathologic report included the sketches of FIGS. 7A–7J and a written description of the observations made of the actual prostate cross sections represented by the sketches of FIGS. 7A–7J.

FIGS. 7A–7J are sketches illustrating the relative area of necrosed tissue within the prostate of Patient 30. Reference numerals have been added to the sketches to identify the urethra 10, the prostate 14, necrosed tissue 100 and nonnecrosed tissue 102. According to this report, and as illustrated in FIGS. 7A–7J, there was extensive non-inflammatory hemorrhagic necrosis involving virtually the entire prostate. The urethral mucosa was largely preserved, although there were areas of mechanical disruption. The remaining urothelium, seen in 10–20% of the lining showed prominent squamous metaplasia without keratinization. There was a submucosal rim of uninvolved tissue measuring about 1 mm beneath the urothelium. Extending in some areas out to near the edge of the prostate, there was hemorrhagic necrosis with "ghost-like" silhouettes of pre-existing nodules of nodular hyperplasia and benign prostatic glands. There was no significant shrinkage of the prostate, but many of the glands were distorted and destroyed. In some areas, only sheets of red blood cells were observed. The glands at the edge showed varying degrees of squamous metaplasia and basal cell hyperplasia, usually with red blood cells in the lumens. The area of necrosis involved the entire transition zone and all of the nodules of nodular hyperplasia, as well as the majority of the peripheral zone. The pure stromal nodules showed less evidence of thermal destruction than the mixed epithelial-stromal nodules, but this observation may not be valid given the increased cellularity invariably observed in stromal nodules. No residual or recurrent adenocarcinoma was seen, and there were no thromboemboli in the specimen. The ejaculatory ducts were involved focally in the hemorrhagic necrosis, with lumenal red blood cells, a finding mirrored in the sections of the seminal vesicles which showed some lumenal dilatation and filling with red cells.

As reported by Dr. Bostwick, the area of hemorrhagic necrosis extended 1.8 cm in greatest dimension from the urethra. The periprostatic soft tissues were uninvolved indicating that the thermal injury is limited to the prostate.

b. Patient 35

Figure 8A:
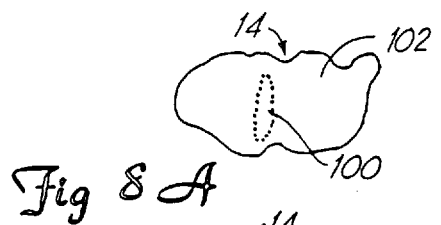
FIGS. 8A–8O are a pictorial representation of a series of cross sections of a prostate of a second patient treated according to the method of the present invention.
Figure 8B:
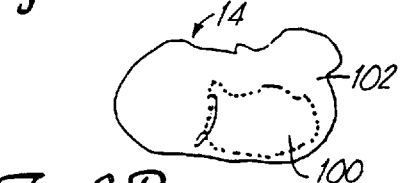
Figure 8C:
Figure 8D:
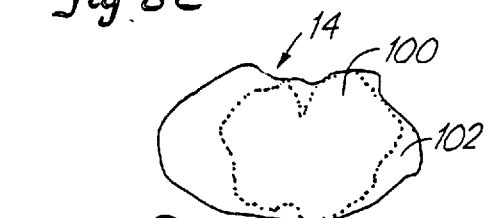
Figure 8E:
Figure 8F:
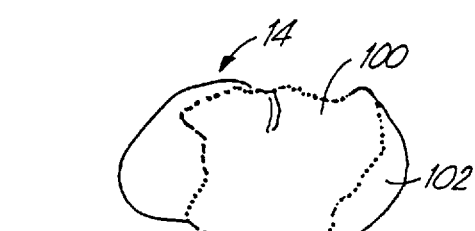
Figure 8G:
Figure 8H:
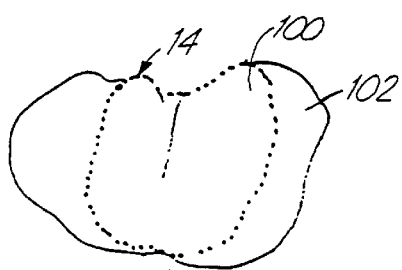
Figure 8I:
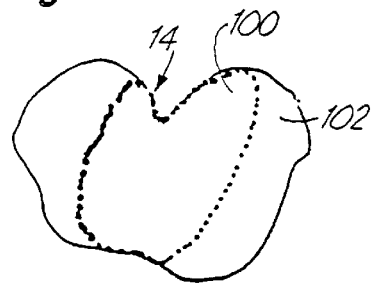
Figure 8J:
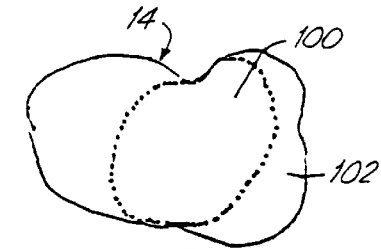
Figure 8K:
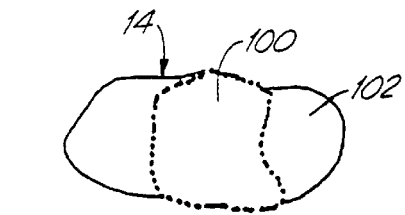
Figure 8L:
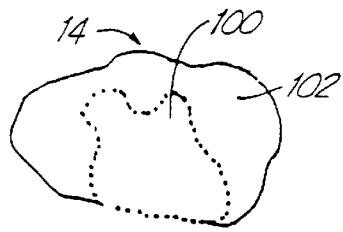
Figure 8M:
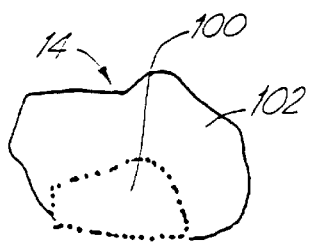
Figure 8N:
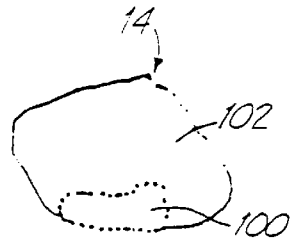
Figure 8O:
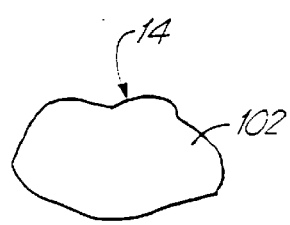

FIGS. 8A–8O illustrate a series of sketches of cross-sections of a prostate harvested from Patient 35 by a prostatic adenectomy some time after treatment under the method of the present invention (illustrated by the procedure in FIG. 6A). The pathologic report on this prostate was rendered by David Bostwick M.D. of Mayo Clinic in Rochester, Minn. This pathologic report included the sketches of FIGS. 8A–8O and a written description of the observations made of the actual prostate cross sections represented by the sketches in FIGS. 8A–8O.

FIGS. 8A–8O are sketches illustrating the relative area of necrosed tissue within the prostate of Patient 35. Reference numerals have been added to the sketches to identify the urethra 10, the prostate 14, necrosed tissue 100 and nonnecrosed tissue 102. According to this report, and as illustrated in FIGS. 8A–8O, there was hemorrhagic necrosis with a minor component of acute and chronic inflammation. At the periphery, the glands showed reactive metaplastic changes and re-epithelialization with basal cell hyperplasia. Large parts of the stroma showed nodules with ghosts of glands indicating complete devitalization. Interestingly, most of the urethral lining was preserved with a 1 mm rim of viable tissue, although parts of the epithelium were denuded d. Summary

These pathology reports demonstrate that the transurethral thermal ablation therapy method of the present invention produces uniform necrosis of intraprostatic tissues at distances of at least 1.8 centimeters from the urethra (e.g., Patient 30) while also preventing necrosis of the urethra (e.g., Patients 30 and 35). The sketches in FIG. 7A–7J, particularly, demonstrate a symmetrical shape and generally constant radius of the necrosed tissue in most cross sections of the prostate.

CONCLUSION

The transurethral thermal ablation therapy method of the present invention produces uniform necrosis within prostatic tissues at distances of at least 1.8 to 2.0 centimeters from the urethra. This necrosis is achieved by maintaining the continuous application of microwave energy within a power range and for a time period sufficient to generate intraprostatic temperatures of at least 45° C. at distances of at least 2 centimeters from the wall of the urethra. This relatively deep, uniform necrosis of intraprostatic tissues encompasses and completely necroses the tumorous tissue within prostates of patients with BPH (or other prostatic diseases) while also preserving the urethra and rectum. In addition, this result can be achieved while focusing more microwave energy and heat to anterior and lateral portions of the prostate (where most tumorous BPH tissue is located) than posterior portions of the prostate. This preferential heating pattern focuses the necrosis onto tumorous tissue while preserving healthy prostatic tissues and surrounding tissues. Ultimately, the method of the present invention will result in more BPH patients having successful treatment performed in a one hour therapy session.

While the beneficial uses of the microwave antenna-containing catheter of the present invention have been described with respect to the urethra, other intracavitary applications are implied. In addition, the method of the present invention can be applied for treating prostatic tissue diseases other than benign prostatic hyperplasia, such as cancer.

Although the present invention has been described with reference to preferred embodiments, workers skilled in the art will recognize that changes may be made in form and detail without departing from the spirit and scope of the invention.

What is claimed is:

1. A method for treating an individual with prostatic tissue disease, the method comprising:

inserting a catheter within a urethra to position a microwave antenna located within the catheter adjacent to a prostate surrounding the urethra;

heating a volume of tissue within the prostate, excluding tissue adjacent the rectal wall, with continuously applied microwave energy from the microwave antenna to temperatures of at least 45° C. up to a distance of at least 2 centimeters from the wall of the urethra for a time period sufficient to destroy substantially the entire volume of tissue while cooling the urethra.

2. The method of claim 1 wherein the step of heating further comprises:

producing an asymmetrical radiation pattern within the prostate with the microwave energy.

3. The method of claim 2 wherein the producing step further comprises:

providing a greater amount of cooling on a first side of the prostate than on a second side of the prostate.

4. The method of claim 2 wherein the producing step further comprises:

locating the microwave antenna within the catheter nearer a first side of the catheter than a second side of the catheter, the first side of the catheter to be positioned adjacent the anterior and lateral portions of the prostate and the second side of the catheter to be positioned adjacent the posterior portion of the prostate.

5. The method of claim 1 and further including:

preventing a temperature of a rectum from exceeding 42° C.

6. A method for treating an individual with prostatic tissue disease, the method comprising:

inserting a catheter within a urethra to position a microwave antenna located within the catheter adjacent to a prostate surrounding the urethra;

circulating a fluid within the catheter to cool the urethra; and applying power to the microwave antenna continuously within a power range and for a time period sufficient to substantially destroy a volume of tissue within the prostate up to at least 1.8 centimeters from the wall of the urethra while cooling the urethra during the application of power and while maintaining a temperature of the rectum below 42° C.

7. A method for treating an individual with prostatic tissue disease, the method comprising:
  inserting a catheter within a urethra to position a microwave antenna located within the catheter adjacent to a prostate surrounding the urethra;
  cooling the urethra with the catheter;
  applying power in increasing levels to the microwave antenna until predetermined criteria are met while continuing to cool the urethra; and
  maintaining power applied to the microwave antenna within a desired power range which causes heating within the prostate to a temperature of at least 45° C. up to at least 2 centimeters from the wall of the urethra for a time sufficient to necrose prostatic tissue while continuing to cool the urethra to prevent necrosis of the urethra.

8. The method of claim 7 wherein the predetermined criteria are met when at least one of the following conditions exist: (1) the catheter temperature reaches a first minimum temperature; and (2) a temperature of a rectum reaches a second minimum temperature.

9. The method of claim 8 wherein the first minimum temperature is 35° C., the second minimum temperature is 40° C., and the minimum power level is 35 Watts.

10. The method of claim 8 wherein the predetermined criteria further includes the catheter temperature reaching a temperature within 1° C. to 40° C.

11. The method of claim 10 wherein the step of maintaining power further comprises maintaining the power level within the desired range to maintain a temperature of the rectum below 42° C.

12. The method of claim 11 wherein maintaining the power level further comprises:
  decreasing the power level in increments of 1 watt per minute if the temperature of the rectum reaches 42° C. until the temperature of the rectum is below 42° C.

13. The method of claim 12 and further comprising:
  increasing the power level in increments of one watt per minute after the temperature of the rectum returns to a temperature below 42° C. until the catheter temperature is within 1° C. of 40° C.

14. The method of claim 7 wherein in the step of maintaining power, the desired power range is selected to cause the catheter temperature to be maintained at some determined temperature level within 1° C. of 40° C.

15. The method of claim 7 wherein in the step of maintaining power, the desired power range is selected to cause the catheter temperature to be maintained at a temperature within 1° C. of 40° C.

16. The method of claim 15 wherein the power is maintained within the desired range by adjusting the power level in one watt increments per minute.

17. The method of claim 7 wherein the step of applying increasing power levels further comprises:
  applying a power level of ten watts for two minutes and then increasing the power level in increments of 5 watts every 2 minutes.

18. The method of claim 17 in the step of applying increasing power levels further comprises:
  increasing the power level in increments of 1 watt per minute after the predetermined criteria are met until the catheter temperature is within 1° C. of 40° C.

19. The method of claim 7 wherein the first step of cooling the urethra further comprises:
  circulating a fluid between the microwave antenna and the urethra at temperature of 10° C. or less for up to 10 minutes prior to the step of applying power.

20. The method of claim 7 wherein the steps of applying power and maintaining power further comprise:
  applying power at a frequency in the range of approximately 902 to 928 MHz to the microwave antenna to apply a MW emission to the portion of the prostate surrounding the catheter.

21. A method for treating an individual with benign prostatic hyperplasia, the method comprising:
  inserting a catheter into a urethra to position a microwave antenna located within the catheter adjacent to a prostate surrounding the urethra;
  cooling the urethra with the catheter;
  applying power in increasing levels to the microwave antenna until predetermined criteria are met while continuing to cool the urethra;
  maintaining power applied to the microwave antenna within a range which causes substantially continuous heating of tissue within the prostate to a temperature of at least 45° C. at a distance of at least 2 centimeters from the urethra while continuing to cool the urethra; and
  cooling the urethra after discontinuing power.

22. A method for treating an individual with benign prostatic hyperplasia, the method comprising:
  measuring a temperature of a rectum;
  inserting a catheter into a urethra to position a microwave antenna located within the catheter adjacent to a prostate surrounding the urethra;
  cooling the urethra with the catheter to maintain the urethra at a non-necrotic temperature;
  applying power in a microwave frequency range to the microwave antenna until an urethral catheter temperature is within a predetermined range so that a portion of the prostate surrounding the microwave antenna reaches a temperature of at least 45° C. at a distance of up to 2 centimeters from the urethra;
  adjusting the power level to continuously maintain the catheter temperature within the predetermined temperature range for a predetermined period of time and to maintain the rectal temperature below a predetermined temperature so that the portion of the prostate is maintained at a substantially continuous temperature of at least 45° C. at a distance of up to 2 centimeters from the urethra for a time sufficient to necrose the portion of the prostate;
  decreasing the power applied to the microwave antenna to zero watts; and
  cooling the urethra with the catheter after decreasing the power.

23. The method of claim 22 wherein the predetermined temperature range of the catheter temperature is a temperature within 1° C. of 40° C.

24. The method of claim 22 wherein the predetermined temperature of the rectum is 42° C.

25. The method of claim 22 wherein the power is adjusted by changing the power level in one watt increments per minute.

26. The method of claim 22 wherein the step of applying increasing power levels further comprises:
  applying a power level of ten watts for two minutes and then increasing the power level in increments of 5 watts every 2 minutes.

27. The method of claim 26 in the step of applying increasing power levels further comprises:

increasing the power level in increments of 1 watt per minute.

28. The method of claim 22 wherein the first step of cooling the urethra further comprises:

circulating fluid between the microwave antenna and the urethra at temperature of 10° C. or less for up to 10 minutes prior to the step of applying power.

29. The method of claim 22 wherein the steps of applying power and maintaining power further comprise:

applying power at a frequency in the range of approximately 902 to 928 MHz to the microwave antenna to apply a MW emission to the portion of the prostate surrounding the catheter.

30. A method for treating an individual with benign prostatic hyperplasia, the method comprising:

inserting a thermal sensing device into a rectum of the patient measuring a rectal temperature;

inserting a catheter into a urethra to position a microwave antenna located within the catheter adjacent to a prostate surrounding the urethra;

circulating a fluid within the catheter between the microwave antenna and the urethra wherein the fluid stabilizes at a temperature of less than 10° C. to maintain the urethra adjacent the antenna at a temperature below 45° C.;

measuring a temperature of the urethral catheter with a thermosensing device positioned within the urethral catheter adjacent the prostate;

driving the microwave antenna at a signal in the range of 902 to 928 MHz and a power of 10 watts to apply a MW emission to a portion of the prostate surrounding the urethral catheter, the MW emission causing molecular excitation of the portion of the prostate surrounding the microwave antenna;

increasing the drive signal applied to the microwave antenna in increments of five watts every two minutes until at least one of the following conditions is achieved: the urethral catheter temperature is at least 35° C.; and the rectal catheter temperature is about 40° C.;

increasing the drive signal in increments of 1 watts per minute until the urethral catheter temperature is within 1° C. of 40° C. so that the portion of the prostate surrounding the microwave antenna reaches a temperature of at least 45° C.;

adjusting the drive signal in one watt increments per minute to maintain the urethral catheter temperature within 1° C. of 40° C. and maintaining the drive signal at this level for at least 45° C. up to 60 minutes from the time the urethral catheter temperature first reaches 37° C. so that the portion of the prostate is necrosed by being maintained continuously at a temperature of at least 45° C. at distances of at least 2 centimeters from the urethra within the prostate along the length of the microwave antenna;

decreasing the drive signal in increments of one watt per minute if the rectal temperature reaches 42° C. until the rectal temperature is less than 42° C. and then increasing the drive signal in increments of one watt per minute until the urethral catheter temperature is within 1° C. of 40° C. and the rectal catheter temperature is less than 42° C.;

decreasing the drive signal to a power level of zero watts; and maintaining circulation of fluid within the urethral catheter between the microwave antenna and the urethra at a temperature of 10° C. or less for at least ten minutes after discontinuing power applied to the microwave antenna.

31. A method for treating an individual with prostatic tissue disease, the method comprising:

inserting a catheter within a urethra to position a microwave antenna located within the catheter adjacent to a prostate surrounding the urethra;

circulating a fluid within the catheter to cool the urethra; and applying power to the microwave antenna within a power range without discontinuing power and for a time period sufficient to cause necrosis of tissue within the prostate at a distance of at least 1.8 centimeters from the urethra while preventing necrosis of the urethra by cooling the urethra during the application of power.

32. A method for treating prostatic tissue disease, the method comprising:

inserting a catheter within a urethra to position a energy producing source within the catheter adjacent to a prostate surrounding the urethra;

heating a volume of tissue within the prostate, excluding tissue adjacent the rectal wall, with continuously applied energy from the energy producing source to temperatures of at least 45° C. up to at least 2 centimeters from a wall of the urethra for a time sufficient to destroy substantially the entire volume of tissue while cooling the urethra.

33. The method of claim 32 wherein the energy producing source is a microwave antenna.

34. A method for treating an individual with prostatic tissue disease, the method comprising:

inserting a catheter within a urethra to position a microwave antenna located within the catheter adjacent to a prostate surrounding the urethra;

circulating a fluid between the microwave antenna and the urethra; and applying power continuously to the microwave antenna within a power range and for a time period sufficient to destroy substantially an entire volume of tissue within the prostate up to a distance of at least 1.8 centimeters from a wall of the urethra while cooling the urethra during the application of power.

35. A method for treating a target tissue comprising:

inserting a probe within a body conduit to position an energy producing source within the probe adjacent to a target tissue located adjacent the body conduit;

heating a volume of the target tissue with continuously applied energy from the energy producing source to temperatures of at least 45° C. up to at least 2 centimeters from a wall of the body conduit for a time sufficient to destroy substantially the entire volume of targeted tissue while cooling the body conduit.

36. A method for treating an individual with prostatic tissue disease, the method comprising:

inserting a catheter within a urethra to position a microwave antenna located within the catheter adjacent to a prostate surrounding the urethra;

heating tissue within the prostate with continuously applied microwave energy from the microwave antenna to temperatures of at least 45° C. at a distance of at least 2 centimeters from a wall of the urethra for a time sufficient to cause necrosis within the prostate without causing necrosis of tissue outside the prostate while cooling the urethra.

* * * * *

UNITED STATES PATENT AND TRADEMARK OFFICE
CERTIFICATE OF CORRECTION

PATENT NO. : 5,843,144
DATED : DECEMBER 1, 1998
INVENTOR(S) : ERIC N. RUDIE ET AL.

It is certified that error appears in the above-identified patent and that said Letters Patent is hereby corrected as shown below:

Title page, [75] Inventors, line 12, delete "Steven", insert --Stephan--

Signed and Sealed this

Thirtieth Day of November, 1999

Attest:

Attesting Officer

Q. TODD DICKINSON

Acting Commissioner of Patents and Trademarks